(12) United States Patent
Argyropoulos et al.

(10) Patent No.: US 6,307,108 B1
(45) Date of Patent: Oct. 23, 2001

(54) METAL-LIGAND COMPLEX CATALYZED PROCESSES

(75) Inventors: John Nicholas Argyropoulos, Scott Depot; Jeffrey Scott Kanel, Hurricane; Michael Leo Tulchinsky; David James Miller, both of Charleston; Donald Lee Morrison, Hurricane; Paul Foley, Barboursville; David Robert Bryant, So. Charleston, all of WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/525,651

(22) Filed: Mar. 15, 2000

(51) Int. Cl.$^7$ ..................................... C07C 45/50
(52) U.S. Cl. .................. 568/454; 568/451; 568/453; 560/177; 558/85; 556/25; 556/13
(58) Field of Search .................. 568/454, 451, 568/453; 560/177; 558/85; 556/13, 25

(56) References Cited

U.S. PATENT DOCUMENTS

| | | |
|---|---|---|
| 3,904,547 | 9/1975 | Aycock et al. . |
| 4,300,002 | 11/1981 | Shibatani et al. . |
| 4,633,021 | 12/1986 | Hanes . |
| 4,845,306 | 7/1989 | Puckette . |
| 5,138,101 | 8/1992 | Devon . |
| 5,180,854 | 1/1993 | Abatjoglou et al. . |
| 5,264,616 | 11/1993 | Roeper et al. . |
| 5,463,082 | 10/1995 | Horvath et al. . |
| 5,648,554 | 7/1997 | Mori et al. . |
| 5,719,312 | 2/1998 | Hansen et al. . |
| 5,756,854 | 5/1998 | Bahrmann et al. . |
| 5,773,666 | 6/1998 | Omatsu et al. . |
| 5,789,625 | 8/1998 | Bryant et al. . |
| 5,847,228 | 12/1998 | Monflier et al. . |
| 5,932,772 | 8/1999 | Argyopoulos et al. . |
| 5,952,530 | 9/1999 | Argyopoulos et al. . |

FOREIGN PATENT DOCUMENTS

| | | |
|---|---|---|
| 0922691A1 | 6/1999 | (EP) . |
| 23850A74 | 6/1975 | (IT) . |
| 9715543 | 5/1997 | (WO) . |
| 9906345 | 2/1999 | (WO) . |

OTHER PUBLICATIONS

Article: Journal of Chemical Society of Japan 9/92, vol. 2 pp. 119–127, New Processes for 1–Octanol and Various Diols Using Noble Metal Complex Catalysts, Yoshimura, N., Y. Tokitoh, M. Matsumoto.

Article: Journal of Am. Chem. Soc. 1993, 115, 2066–2068, Practical, High–Yeild Regioselective, Phodium–Catalyzed Hydroformylation of Functionalized A–Oledfins, Gregory D. Cuny and Stephen L. Buchwald.

Primary Examiner—Paul J. Killos
(74) Attorney, Agent, or Firm—Warren K. Volles

(57) ABSTRACT

This invention relates to a process for separating one or more organophosphorus ligand degradation products, one or more reaction byproducts and one or more formylester products from a reaction product fluid comprising one or more unreacted unsaturated ester reactants, a metal-organophoshorus ligand complex catalyst, optionally free organophosphorus ligand, said one or more organophosphorus ligand degradation products, said one or more reaction byproducts, said one or more products, a nonpolar solvent and a polar solvent by phase separation wherein (i) the selectivity of the nonpolar phase for the organophosphorus ligand with respect to the one or more products is expressed by a partition coefficient ratio Ef1 which is a value greater than about 2.5 (ii) the selectivity of the nonpolar phase for the organophosphorus ligand with respect to the one or more organophosphorus ligand degradation products is expressed by a partition coefficient ratio Ef2 which is a value greater than about 2.5, and (iii) the selectivity of the nonpolar phase for the organophosphorus ligand with respect to the one or more reaction byproducts is expressed by a partition coefficient ratio Ef3 which is a value greater than about 2.5.

24 Claims, No Drawings

METAL-LIGAND COMPLEX CATALYZED PROCESSES

RELATED APPLICATION

This application is related to copending U.S. patent application Ser. No. (D-17979), filed on an even date herewith, the disclosure of which is incorporated herein by reference.

BRIEF DESCRIPTION OF THE INVENTION

Technical Field

This invention relates to improved metal-organophosphorus ligand complex catalyzed processes. More particularly this invention relates to metal-organophosphorus ligand complex catalyzed processes in which the desired product, along with any organophosphorus ligand degradation products and reaction byproducts, can be selectively extracted and separated from the reaction product fluid by phase separation.

BACKGROUND OF THE INVENTION

It is known in the art that various products may be produced by reacting one or more reactants in the presence of an metal-organophosphorus ligand complex catalyst. However, stabilization of the catalyst and organophosphorus ligand remains a primary concern of the art. Obviously catalyst stability is a key issue in the employment of any catalyst. Loss of catalyst or catalytic activity due to undesirable reactions of the highly expensive metal catalysts can be detrimental to the production of the desired product. Moreover, production costs of the product obviously increase when productivity of the catalyst decreases.

For instance, a cause of organophosphorus ligand degradation and catalyst deactivation of metal-organophosphorus ligand complex catalyzed hydroformylation processes is due in part to vaporizer conditions present during, for example, in the vaporization employed in the separation and recovery of the aldehyde product from the reaction product mixture. When using a vaporizer to facilitate separation of the aldehyde product of the process, a harsh environment of a high temperature and a low carbon monoxide partial pressure than employed during hydroformylation is created, and it has been found that when a organophosphorus promoted rhodium catalyst is placed under such vaporizer conditions, it will deactivate at an accelerated pace with time. It is further believed that this deactivation is likely caused by the formation of an inactive or less active rhodium species. Such is especially evident when the carbon monoxide partial pressure is very low or absent. It has also been observed that the rhodium becomes susceptible to precipitation under prolonged exposure to such vaporizer conditions.

For instance, it is theorized that under harsh conditions such as exist in a vaporizer, the active catalyst, which under hydroformylation conditions is believed to comprise a complex of rhodium, organophosphorus ligand, carbon monoxide and hydrogen, loses at least some of its coordinated carbon monoxide, thereby providing a route for the formation of such a catalytically inactive or less active rhodium. Accordingly, a successful method for preventing and/or lessening such degradation of the organophosphorus ligand and deactivation of the catalyst as occur under harsh separation conditions in a vaporizer would be highly desirable to the art.

Organophosphorus ligand degradation and catalyst deactivation of metal-organophosphorus ligand complex catalyzed hydroformylation processes can occur under process conditions other than vaporizer conditions. The buildup of organophosphorus ligand degradation products as well as reaction byproducts in the reaction product fluid can have a detrimental effect on the process, e.g., decreases catalyst efficiency, raw material conversion and product selectivity. Accordingly, a successful method for preventing and/or lessening such buildup of organophosphorus ligand degradation products and reaction byproducts in the reaction product fluid would be highly desirable in the art.

DISCLOSURE OF THE INVENTION

It has now been discovered that in metal-organophosphorus ligand complex catalyzed processes, the desired product, along with any organophosphorus ligand degradation products and reaction byproducts, can be selectively extracted and separated from the reaction product fluid by phase separation. By the practice of this invention, it is now possible to separate the desired product, along with any organophosphorus ligand degradation products and reaction byproducts, from the reaction product fluid without the need to use vaporization separation and the harsh conditions associated therewith. This invention provides a highly desirable separation method which prevents and/or lessens degradation of the organophosphorus ligand and deactivation of the catalyst as occur under harsh conditions with vaporization separation. This invention also provides a highly desirable separation method which prevents and/or lessens the buildup of organophosphorus ligand degradation products and reaction byproducts in the reaction product fluid.

This invention relates in part to a process for separating one or more organophosphorus ligand degradation products, one or more reaction byproducts and one or more products, said products comprising one or more formylesters and/or derivatives thereof, from a reaction product fluid comprising one or more unreacted unsaturated reactants, said unsaturated reactants comprising one or more unsaturated esters and/or derivatives thereof, a metal-organophosphorus ligand complex catalyst, optionally free organophosphorus ligand, said one or more organophosphorus ligand degradation products, said one or more reaction byproducts, said one or more products, a nonpolar solvent and a polar solvent, wherein said process comprises (1) mixing said reaction product fluid to obtain by phase separation a nonpolar phase comprising said one or more unreacted unsaturated reactants, said metal-organophosphorus ligand complex catalyst, said optionally free organophosphorus ligand and said nonpolar solvent and a polar phase comprising said one or more organophosphorus ligand degradation products, said one or more reaction byproducts, said one or more products and said polar solvent, and (2) recovering said polar phase from said nonpolar phase; wherein (i) the selectivity of the nonpolar phase for the organophosphorus ligand with respect to the one or more products is expressed by the following partition coefficient ratio Ef1:

$$Ef1 = \frac{\text{Partition coefficient } Kp1 \text{ of organophosphorus ligand}}{\text{Partition coefficient } Kp2 \text{ of one or more products}}$$

in which said partition coefficient Kp1 is the ratio of the concentration of organophosphorus ligand in the nonpolar phase after extraction to the concentration of organophosphorus ligand in the polar phase after extraction, said partition coefficient Kp2 is the ratio of the concentration of products in the nonpolar phase after extraction to the concentration of products in the polar phase after extraction, and said Ef1 is a value greater than about 2.5, (ii) the selectivity of the nonpolar phase for the organophosphorus ligand with respect to the one or more organophosphorus ligand degradation products is expressed by the following partition coefficient ratio Ef2:

$$Ef2 = \frac{\text{Partition coefficient } Kp1 \text{ of organophosphorus ligand}}{\text{Partition coefficient } Kp3 \text{ of one or more organophosphorus ligand degradation products}}$$

in which said partition coefficient Kp1 is as defined above, said partition coefficient Kp3 is the ratio of the concentration of organophosphorus ligand degradation products in the nonpolar phase after extraction to the concentration of organophosphorus ligand degradation products in the polar phase after extraction, and said Ef2 is a value greater than about 2.5, and (iii) the selectivity of the nonpolar phase for the organophosphorus ligand with respect to the one or more reaction byproducts is expressed by the following partition coefficient ratio Ef3:

$$Ef3 = \frac{\text{Partition coefficient } Kp1 \text{ of organophosphorus ligand}}{\text{Partition coefficient } Kp4 \text{ of one or more reaction byproducts}}$$

in which said partition coefficient Kp1 is as defined above, said partition coefficient Kp4 is the ratio of the concentration of reaction byproducts in the nonpolar phase after extraction to the concentration of reaction byproducts in the polar phase after extraction, and said Ef3 is a value greater than about 2.5.

This invention also relates in part to a process for separating one or more organophosphorus ligand degradation products, one or more reaction byproducts and one or more products, said products comprising one or more formylesters and/or derivatives thereof, from a reaction product fluid comprising one or more unreacted unsaturated reactants, said unsaturated reactants comprising one or more unsaturated esters and/or derivatives thereof, a metal-organophosphorus ligand complex catalyst, optionally free organophosphorus ligand, said one or more organophosphorus ligand degradation products, said one or more reaction byproducts, said one or more products and a nonpolar solvent, wherein said process comprises (1) mixing said reaction product fluid with a polar solvent to obtain by phase separation a nonpolar phase comprising said one or more unreacted unsaturated reactants, said metal-organophosphorus ligand complex catalyst, said optionally free organophosphorus ligand and said nonpolar solvent and a polar phase comprising said one or more organophosphorus ligand degradation products, said one or more reaction byproducts, said one or more products and said polar solvent, and (2) recovering said polar phase from said nonpolar phase; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention further relates in part to a process for producing one or more products, said products comprising one or more formylesters and/or derivatives thereof, comprising: (1) reacting one or more unsaturated reactants, said unsaturated reactants comprising one or more unsaturated esters and/or derivatives thereof, in the presence of a metal-organophosphorus ligand complex catalyst, optionally free organophosphorus ligand, a nonpolar solvent and a polar solvent to form a multiphase reaction product fluid, and (2) separating said multiphase reaction product fluid to obtain at least one nonpolar phase comprising one or more unreacted unsaturated reactants, said metal-organophosphorus ligand complex catalyst, said optionally free organophosphorus ligand and said nonpolar solvent and at least one polar phase comprising one or more organophosphorus ligand degradation products, one or more reaction byproducts, said one or more products and said polar solvent; wherein (i) the selectivity of the at least one nonpolar phase for the organophosphorus ligand with respect to the one or more products is expressed by the partition coefficient ratio Ef1 defined above which is a value greater than about 2.5, (ii) the selectivity of the at least one nonpolar phase for the organophosphorus ligand with respect to the one or more organophosphorus ligand degradation products is expressed by the partition coefficient ratio Ef2 defined above which is a value greater than about 2.5, and (iii) the selectivity of the at least one nonpolar phase for the organophosphorus ligand with respect to the one or more reaction byproducts is expressed by the partition coefficient ratio Ef3 defined above which is a value greater than about 2.5.

This invention yet further relates in part to a process for producing one or more products, said products comprising one or more formylesters and/or derivatives thereof, comprising: (1) reacting one or more unsaturated reactants, said unsaturated reactants comprising one or more unsaturated esters and/or derivatives thereof, in the presence of a metal-organophosphorus ligand complex catalyst, optionally free organophosphorus ligand and a nonpolar solvent to form a reaction product fluid; (2) mixing said reaction product fluid with a polar solvent to form a multiphase reaction product fluid; and (3) separating said multiphase reaction product fluid to obtain at least one nonpolar phase comprising one or more unreacted unsaturated reactants, said metal-organophosphorus ligand complex catalyst, said optionally free organophosphorus ligand and said nonpolar solvent and at least one polar phase comprising one or more organophosphorus ligand degradation products, one or more reaction byproducts, said one or more products and said polar solvent; wherein (i) the selectivity of the at least one nonpolar phase for the organophosphorus ligand with respect to the one or more products is expressed by the partition coefficient ratio Ef1 defined above which is a value greater than about 2.5, (ii) the selectivity of the at least one nonpolar phase for the organophosphorus ligand with respect to the one or more organophosphorus ligand degradation products is expressed by the partition coefficient ratio Ef2 defined above which is a value greater than about 2.5, and (iii) the selectivity of the at least one nonpolar phase for the organophosphorus ligand with respect to the one or more reaction byproducts is expressed by the partition coefficient ratio Ef3 defined above which is a value greater than about 2.5.

This invention relates in part to a process for separating one or more organophosphorus ligand degradation products, one or more reaction byproducts and one or more products, said products comprising one or more formylesters and/or derivatives thereof, from a reaction product fluid comprising one or more unreacted unsaturated reactants, said unsaturated reactants comprising one or more unsaturated esters and/or derivatives thereof, a metal-organophosphorus ligand complex catalyst, optionally free organophosphorus ligand, said one or more organophoshorus ligand degradation products, said one or more reaction byproducts, said one or more products, a first nonpolar solvent and a second nonpolar solvent, wherein said process comprises (1) mixing said reaction product fluid to obtain by phase separation a nonpolar phase comprising said one or more unreacted unsaturated reactants, said metal-organophosphorus ligand complex catalyst, said optionally free organophosphorus ligand, said first nonpolar solvent and said second nonpolar solvent and a polar phase comprising said one or more organophosphorus ligand degradation products, said one or more reaction byproducts and said one or more products, and (2) recovering said polar phase from said nonpolar phase; wherein (i) the selectivity of the nonpolar phase for the organophosphorus ligand with respect to the one or more products is expressed by the partition coefficient ratio Ef1 defined above which is at value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention also relates in part to a process for separating one or more organophosphorus ligand degradation products, one or more reaction byproducts and one or more products, said products comprising one or more formylesters and/or derivatives thereof from a reaction product fluid comprising one or more unreacted unsaturated reactants, said unsaturated reactants comprising one or more unsaturated esters and/or derivatives thereof, a metal-organophosphorus ligand complex catalyst, optionally free organophosphorus ligand, said one or more organophosphorus ligand degradation products, said one or more reaction byproducts, said one or more products and a first nonpolar solvent, wherein said process comprises (1) mixing said reaction product fluid with a second nonpolar solvent to obtain by phase separation a nonpolar phase comprising said one or more unreacted unsaturated reactants, said metal-organophosphorus ligand complex catalyst, said optionally free organophosphorus ligand, said first nonpolar solvent and said second nonpolar solvent and a polar phase comprising said one or more organophosphorus ligand degradation products, said one or more reaction byproducts and said one or more products, and (2) recovering said polar phase from said nonpolar phase; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophoshorus ligand with respect to the one or more reaction byproducts is expressed by the partition coefficient ratio Ef3 defined above which is a value greater than about 2.5.

This invention further relates in part to a process for producing one or more products, said products comprising one or more formylesters and/or derivatives thereof, comprising: (1) reacting one or more unsaturated reactants, said unsaturated reactants comprising one or more unsaturated esters and/or derivatives thereof, in the presence of a metal-organophoshorus ligand complex catalyst, optionally free organophosphorus ligand, a first nonpolar solvent and a second nonpolar solvent to form a multiphase reaction product fluid; and (2) separating said multiphase reaction product fluid to obtain at least one nonpolar phase comprising one or more unreacted unsaturated reactants, said metal-organophosphorus ligand complex catalyst, said optionally free organophosphorus ligand, said first nonpolar solvent and said second nonpolar solvent and at least one polar phase comprising one or more organophosphorus ligand degradation products, one or more reaction byproducts and said one or more products; wherein (i) the selectivity of the at least one nonpolar phase for the organophosphorus ligand with respect to the one or more products is expressed by the partition coefficient ratio Ef1 defined above which is a value greater than about 2.5, (ii) the selectivity of the at least one nonpolar phase for the organophosphorus ligand with respect to the one or more organophosphorus ligand degradation products is expressed by the partition coefficient ratio Ef2 defined above which is a value greater than about 2.5, and (iii) the selectivity of the at least one nonpolar phase for the organophosphorus ligand with respect to the one or more reaction byproducts is expressed by the partition coefficient ratio Ef3 defined above which is a value greater than about 2.5.

This invention yet further relates in part to a process for producing one or more products, said products comprising one or more formylesters and/or derivatives thereof, comprising: (1) reacting one or more unsaturated reactants, said unsaturated reactants comprising one or more unsaturated esters and/or derivatives thereof, in the presence of a metal-organophosphorus ligand complex catalyst, optionally free organophosphorus ligand and a first nonpolar solvent to form a reaction product fluid; (2) mixing said reaction product fluid with a second nonpolar solvent to form a multiphase reaction product fluid; and (3) separating said multiphase reaction product fluid to obtain at least one nonpolar phase comprising one or more unreacted unsaturated reactants, said metal-organophosphorus ligand complex catalyst, said optionally free organophosphorus ligand, said first nonpolar solvent and said second nonpolar solvent and at least one polar phase comprising one or more organophosphorus ligand degradation products, one or more reaction byproducts and said one or more products; wherein (i) the selectivity of the at least one nonpolar phase for the organophosphorus ligand with respect to the one or more products is expressed by the partition coefficient ratio Ef1 defined above which is a value greater than about 2.5, (ii) the selectivity of the at least one nonpolar phase for the organophosphorus ligand with respect to the one or more organophosphorus ligand degradation products is expressed by the partition coefficient ratio Ef2 defined above which is a value greater than about 2.5, and (iii) the selectivity of the at least one nonpolar phase for the organophosphorus ligand with respect to the one or more reaction byproducts is expressed by the partition coefficient ratio Ef3 defined above which is a value greater than about 2.5.

This invention relates in part to a process for separating one or more organophosphorus ligand degradation products, one or more reaction byproducts and one or more products, said products comprising one or more formylesters and/or derivatives thereof, from a reaction product fluid comprising one or more unreacted unsaturated reactants, said unsaturated reactants comprising one or more unsaturated esters and/or derivatives thereof, a metal-organophosphorus ligand complex catalyst, optionally free organophosphorus ligand, said one or more organophosphorus ligand degradation products, said one or more reaction byproducts, said one or more products and a nonpolar solvent, wherein said process comprises (1) mixing said reaction product fluid to obtain by phase separation a nonpolar phase comprising said one or more unreacted unsaturated reactants, said metal-organophosphorus ligand complex catalyst, said optionally free organophosphorus ligand and said nonpolar solvent and a polar phase comprising said one or more organophosphorus ligand degradation products, said one or more reaction byproducts and said one or more products, and (2) recovering said polar phase from said nonpolar phase; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention also relates in part to a process for producing one or more products, said products comprising one or more formylesters and/or derivatives thereof, comprising: (1) reacting one or more unsaturated reactants, said unsaturated reactants comprising one or more unsaturated esters and/or derivatives thereof, in the presence of a metal-organophosphorus ligand complex catalyst, optionally free organophosphorus ligand and a nonpolar solvent to form a multiphase reaction product fluid; and (2) separating said multiphase reaction product fluid to obtain at least one nonpolar phase comprising one or more unreacted unsaturated reactants, said metal-organophosphorus ligand complex catalyst, said optionally free organophosphorus ligand and said nonpolar solvent and at least one polar phase comprising one or more organophosphorus ligand degradation products, one or more reaction byproducts and said one or more products; wherein (i) the selectivity of the at least one nonpolar phase for the organophosphorus ligand with respect to the one or more products is expressed by the partition coefficient ratio Ef1 defined above which is a value greater than about 2.5, (ii) the selectivity of the at least one nonpolar phase for the organophosphorus ligand with respect to the one or more organophosphorus ligand degradation products is expressed by the partition coefficient ratio Ef2 defined above which is a value greater than about 2.5, and (iii) the selectivity of the at least one nonpolar phase for the organophosphorus ligand with respect to the one or more reaction byproducts is expressed by the partition coefficient ratio Ef3 defined above which is a value greater than about 2.5.

DETAILED DESCRIPTION

The processes of this invention may be asymmetric or non-asymmetric, the preferred processes being non-asymmetric, and may be conducted in any continuous or semi-continuous fashion. The extraction and separation are critical features of this invention and may be conducted as described herein. The processing techniques used in this invention may correspond to any of the known processing techniques heretofore employed in conventional processes. Likewise, the manner or order of addition of the reaction ingredients and catalyst are also not critical and may be accomplished in any conventional fashion. As used herein, the term "reaction product fluid" is contemplated to include, but not limited to, a reaction mixture containing an amount of any one or more of the following: (a) a metal-organophosphorus ligand complex catalyst, (b) free organophosphorus ligand, (c) product(s), organophosphorus ligand degradation product(s) and byproduct(s) formed in the reaction, (d) unreacted reactant(s), and (e) solvent(s). By the practice of this invention, it is now possible to extract and separate the one or more products, organophosphorus ligand degradation products and reaction byproducts from the metal-organophosphorus ligand complex catalyst and unreacted reactants without the need to use vaporization separation and the harsh conditions associated therewith. As used herein, the term "organophosphorus ligand degradation products" is contemplated to include, but not limited to, any and all products resulting from the degradation of free organophosphorus ligand and organophosphorus ligand complexed with metal, e.g., phosphorus-containing acids, aldehyde acids, and the like. As used herein, the term "reaction byproducts" is contemplated to include, but not limited to, any and all byproducts resulting from the reaction of one or more reactants to give one or more products, e.g., product dimers, product trimers, isomerization products, hydrogenation products, and the like.

Hyxdroformylation Step or Stage

The hydroformylation process involves converting one or more substituted or unsubstituted unsaturated esters, e.g., esters of undecenoic acid such as esters of 10-undecenoic acid, to one or more substituted or unsubstituted formylesters, e.g., formylundecanoates such as 11-formylundecanoates, in one or more steps or stages. As used herein, the term "hydroformylation" is contemplated to include, but is not limited to, all permissible hydroformylation processes which involve converting one or more substituted or unsubstituted unsaturated esters, e.g., esters of undecenoic acid, to one or more substituted or unsubstituted formylesters, e.g., formylundecanoates. In general, the hydroformylation step or stage comprises reacting one or more substituted or unsubstituted unsaturated esters, e.g., esters of undecenoic acid, with carbon monoxide and hydrogen in the presence of a hydroformylation catalyst to produce one or more substituted or unsubstituted formylesters, e.g., formylundecanoates. Preferred processes are those involving catalyst liquid recycle hydroformylation processes.

In general, such catalyst liquid recycle hydroformylation processes involve the production of aldehydes by reacting an olefinic unsaturated compound with carbon monoxide and hydrogen in the presence of a metal-organophosphorus ligand complex catalyst in a liquid medium that also contains a solvent for the catalyst and ligand. Preferably free organophosphorus ligand is also present in the liquid hydroformylation reaction medium. The recycle procedure generally involves withdrawing a portion of the liquid reaction medium containing the catalyst and aldehyde product from the hydroformylation reactor (i.e., reaction zone), either continuously or intermittently, and recovering the aldehyde product therefrom in accordance with the separation techniques of this invention.

In a preferred embodiment, the hydroformylation reaction mixtures employable herein includes any mixture derived from any corresponding hydroformylation process that contains at least some amount of four different main ingredients or components i.e., the formylester product, a metal-organophosphorus ligand complex catalyst, free organophosphorus ligand and an organic solubilizing agent, e.g., nonpolar solvent, for said catalyst and said free ligand, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation byproducts, as well as other inert co-solvent, e.g., polar solvent, type materials or hydrocarbon additives, if employed.

The substituted or unsubstituted olefin reactants that may be employed in the hydroformylation processes include both optically active (prochiral and chiral) and non-optically active (achiral) esters of undecenoic acid. Such olefinic unsaturated compounds can be terminally or internally unsaturated and be of straight-chain, branched chain or cyclic structures, as well as olefin mixtures. Moreover, mixtures of two or more different olefinic unsaturated compounds may be employed as the starting material if desired. Preferably, the esters of undecenoic acid are prepared from castor oil by transesterification of the triglyceride with an alcohol, followed by pyrolysis of the resulting ricinolic acid ester to give heptanal and the desired ester of 10-undecenoic acid. Alternatively, the esters of undecenoic acid are prepared from castor oil by cracking castor oil to obtain 3 equivalents of heptanal and 1 equivalent of a triglyceride with triple unsaturation which can be hydroformylated to the desired ester of 10-undecenoic acid. See, for example, Kirk-Othmer, Encyclopedia of Chemical Technology, Fourth Edition, 1996, Vol. 5), pp. 302–320.

Preferred unsaturated reactants include unsaturated esters and/or derivatives thereof. As used herein, derivatives of unsaturated esters include, for example, unsaturated acids and salts of the unsaturated acids. This invention is not intended to be limited in any manner by the permissible derivatives of unsaturated esters.

Preferred unsaturated esters include esters of undecenoic acid represented by the formula

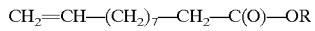

$$CH_2=CH-(CH_2)_7-CH_2-C(O)-OR$$

wherein R is hydrogen or a substituted or unsubstituted hydrocarbon having a carbon atom number sufficient to render said unsaturated ester miscible in a nonpolar solvent. Typically, R contains from 1 to about 6 or 7 carbon atoms.

Illustrative of suitable substituted and unsubstituted olefinic starting materials include those permissible substituted and unsubstituted unsaturated esters, including esters of undecenoic acid, described in Beilsteins Handbuch der Organischen Chemie, Springer Verlag KG, 4$^{th}$ Edition, the pertinent portions of which are incorporated herein by reference.

Illustrative metal-organophosphorus ligand complex catalysts employable in the processes encompassed by this invention as well as methods for their preparation are well known in the art and include those disclosed in the below mentioned patents. In general such catalysts may be preformed or formed in situ as described in such references and consist essentially of metal in complex combination with an organophosphorus ligand. The active species may also contain carbon monoxide and/or hydrogen directly bonded to the metal.

The catalyst useful in the processes includes a metal-organophosphorus ligand complex catalyst which can be optically active or non-optically active. The permissible metals which make up the metal-organophosphorus ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group 11 metals selected from copper (Cu), silver (Ag), gold (Au) and mixtures thereof, and also Group 6 metals selected from chromium (Cr), molybdenum (Mo), tungsten (W) and mixtures thereof. Mixtures of metals from Groups 6, 8, 9, 10 and 11 may also be used in this invention. The permissible organophosphorus ligands which make up the metal-organophosphorus ligand complexes and free organophosphorus ligand include organophosphines, e.g., bisphosphines and triorganophosphines, and organophosphites, e.g., mono-, di-, tri- and polyorganophosphites. Other permissible organophosphorus ligands include, for example, organophosphonites, organophosphinites, organophosphorus amides and the like. Mixtures of such ligands may be employed if desired in the metal-organophosphorus ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-organophosphorus ligand complex species, which may be present in their mononuclear, dinuclear and/or higher nuclearity forms. Indeed, the exact structure is not known. Although it is not intended herein to be bound to any theory of mechanistic discourse, it appears that the catalytic species may in its simplest form consist essentially of the metal in complex combination with the organophosphorus ligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorus ligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_{3O}$, $CH_2=CHCH_2$, $CH_3CH=CHCH_2$, $C_6H_5$, CN, $CH_3CN$, NO, $NH_3$, pyridine, $(C_2H_5)_3N$, monoolefins, diolefins and triolefins, tetrahydrofuran, and the like. It is of course to be understood that the complex species are preferably free of any additional organic ligand or anion that might poison the catalyst or have an undue adverse effect on catalyst performance. It is preferred in the metal-organophosphorus ligand complex catalyzed processes, e.g., hydroformylation, that the active catalysts be free of halogen and sulfur directly bonded to the metal, although such may not be absolutely necessary. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one organophosphorus-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphorus ligands in view of the carbon monoxide and hydrogen gas employed by the hydroformylation reaction.

The organophosphines and organophosphites that may serve as the ligand of the metal-organophosphorus ligand complex catalyst and/or free ligand of the processes of this invention may be of the achiral (optically inactive) or chiral (optically active) type and are well known in the art. By "free ligand" is meant ligand that is not complexed with (tied to or bound to) the metal, e.g., metal atom, of the complex catalyst. As noted herein, the processes of this invention and especially the hydroformylation process may be carried out in the presence of free organophosphorus ligand. Achiral organophosphines and organophosphites are preferred.

Among the organophosphines that may serve as the ligand of the metal-organophosphine complex catalyst and/or free organophosphine ligand of the reaction mixture starting materials are triorganophosphines, trialkylphosphines, alkyldiarylphosphines, dialkylarylphosphines, dicycloalkylarylphosphines, cycloalkyldiarylphosphines, trialkylphosphines, trialkarylphosphines, tricycloalkylphosphines, and triarylphosphines, alkyl and/or aryl bisphosphines and bisphosphine mono oxides, and the like. Of course any of the hydrocarbon radicals of such tertiary non-ionic organophosphines may he substituted if desired, with any suitable substituent that does not unduly adversely affect the desired result of the hydroformylation reaction. The organophosphine ligands employable in the reactions and/or methods for their preparation are known in the art.

Illustrative triorganophosphine ligands may be represented by the formula:

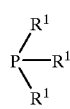

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, for example, alkyl radicals, alkoxy radicals, silyl radicals such as —$Si(R^2)_3$; amino radicals such as —$N(R^2)_2$; acyl radicals such as —$C(O)R^2$; carboxy radicals such as —$C(O)OR^2$; acyloxy radicals such as —$C(O)R^2$; amido radicals such as —$C(O)N(R^2)_2$ and —$N(R^2)C(O)R^2$; sulfonyl radicals such as —$SO_2R^2$; ether radicals such as —$OR^2$; sulfinyl radicals such as —$SOR^2$; sulfenyl radicals such as —$SR_2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —$N(R^2)_2$, each $R^2$ taken together can also represent a divalent bridging group that forms a heterocyclic radical with the nitrogen atom and in amido substituents such as $C(O)N(R^2)_2$ and —$N(R^2)C(O)R^2$ each —$R^2$ bonded to N can also be hydrogen. Illustrative alkyl radicals include, for example, methyl, ethyl, propyl, butyl and the like. Illustrative aryl radicals include, for example, phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl methoxyethylphenyl, acetamidophenyl, dimethylcarbamylphenyl, tolyl, xylyl, and the like.

Illustrative specific organophosphines include, for example triphenylphosphine, tris-p-tolyl phosphine, tris-p-methoxyphenylphosphine, tris-p-fluorophenylphosphine, tris-p)-chlorophenylphosphine, tris-dimethylaminophenylphosphine, propyldiphenylphosphine, t-butyldiphenylphosphine, butyldiphenylphosphine, n-hexyldiphenylphoshine, cyclohexyldiphenylphosphine, dicyclohexylphenylphosphine, tricyclohexylphosphine, tribenzylphosphine as well as the alkali and alkaline earth metal salts of sulfonated triphenylphosphines, for example, of (tri-m-sulfophenyl)phosphine and of (m-sulfophenyl) diphenyl-phosphine and the like.

More particularly, illustrative metal-organophosphine complex catalysts and illustrative free organophosphine ligands include, for example, those disclosed in U.S. Pat. Nos. 3,527,8099; 4,148,830; 4,247,486; 4,283,562; 4,400, 548; 4,482,749 and 4,861,918, the disclosures of which are incorporated herein by reference.

Among the organophosphites that may serve as the ligand of the metal-organophosphite complex catalyst and/or free organophosphite ligand of the reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

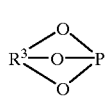

(II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306, the disclosure of which is incorporated herein by reference.

Representative diorganophosphites may include those having the formula:

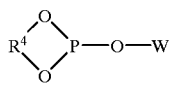

(III)

wherein R⁴ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by R⁴ include divalent acyclic radicals and divalent aromatic radicals. Illustrative divalent acyclic radicals include, for example, alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, for example, in U.S. Pat. Nos. 3,415,906 and 4,567,302 and the like, the disclosures of which are incorporated herein by reference. Illustrative divalent aromatic radicals include, for example, arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably R⁴ is a divalent aromatic radical such as disclosed more fully, for example, in U.S. Pat. Nos. 4,599,206 and 4,717,775, and the like, the disclosures of which ale incorporated herein by reference.

Representative of a more preferred class of diorganophosphites are those of the formula:

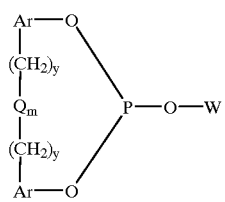

(IV)

wherein W is as defined above, each Ar is the same or different and represents a substituted or unsubstituted aryl radical, each y is the same or different and is a value of 0 or 1, Q represents a divalent bridging group selected from —C(R⁵)₂—, —O—, —S—, —NR⁶⁻, Si(R⁷)₂— and —CO—, wherein each R⁵ is the same or different and represents hydrogen, alkyl radicals having from 1 to 12 carbon atoms, phenyl, tolyl, and anisyl, R⁶ represents hydrogen or a methyl radical, each R⁷ is the same or different and represents hydrogen or a methyl radical, and m is a value of 0 or 1. Such diorganophosphites are described in greater detail, for example, in U.S. Pat. Nos. 4,599,206, 4,717,775 and 4,835,299, the disclosures of which are incorporated herein by reference.

Representative triorganophosphites may include those having the formula:

(V)

wherein each R⁸ is the same or different and is a substituted or unsubstituted monovalent hydrocarbon radical e.g., an alkyl, cycloalkyl, aryl, alkaryl and aralkyl radicals which may contain from 1 to 24 carbon atoms. Suitable hydrocarbon radicals may contain from 1 to 24 carbon atoms or greater and may include those described above for R¹ in formula (I). Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, dimethylphenyl phosphite, diethylphenyl phosphite, methyldiphenyl phosphite, ethyldiphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)(4-biphenyl)phosphite, bis(3,6,8-tri-t-butyl-2-naphthyl)phenylphosphite, bis(3,6,8-tri-t-butyl-2-naphthyl)(4-benzoylphenyl)phosphite, bis(3,6,8-tri-t-butyl-2-naphthyl) (4-sulfonylphenyl)phosphite, and the like. A preferred triorganophosphite is triphenylphosphite. Such triorganophosphites are described in greater detail, for example, in U.S. Pat. Nos. 3,527,809 and 5,277,532, the disclosures of which are incorporated herein by reference.

Representative organopolyphosphites contain two or more tertiary (trivalent) phosphorus atoms and may include those having the formula:

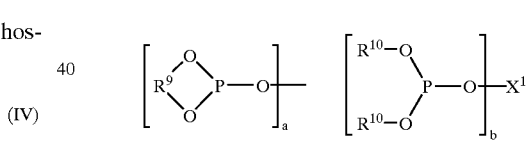

(VI)

wherein X¹ represents a substituted or unsubstituted n-valent hydrocarbon bridging radical containing from 2 to 40 carbon atoms, each R⁹ is the same or different and is a divalent hydrocarbon radical containing from 4 to 40 carbon atoms, each R¹⁰ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each R⁹ radical may be the same or different, and when b has a value of 1 or more, each R¹⁰ radical may also be the same or different.

Representative n-valent (preferably divalent) hydrocarbon bridging radicals represented by X¹, as well as representative divalent hydrocarbon radicals represented by R⁹ above, include both acyclic radicals and aromatic radicals, such as alkylene, alkylene-$Q_m$-alkylene, cycloalkylene, arylene, bisarylene, arylene-alkylene, and arylene-$(CH_2)_y$—$Q_m$—$(CH_2)_y$-arylene radicals, and the like, wherein Q, m and y are as defined above for formula (V). The more preferred acyclic radicals represented by X¹ and R⁹ above are divalent alkylene radicals, while the more preferred aromatic radicals represented by $X^1$ and $R^9$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

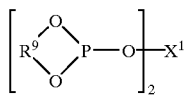

(VII)

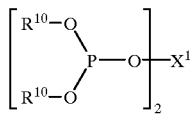

(VIII)

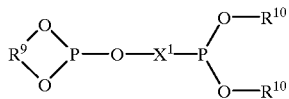

(IX)

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Organophosphite ligands of such Formulas (VI) to (IX) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996: 5,364,950; and 5,391,801; the disclosures of all of which are incorporated herein by reference.

Representative of more preferred classes of organobisphosphites are those of the following formulas (X) to (XII):

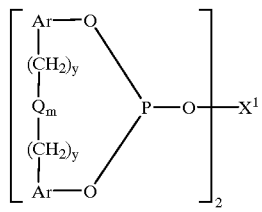

(X)

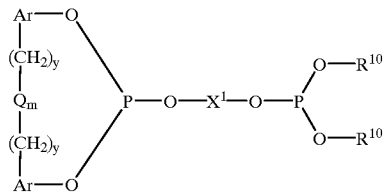

(XI)

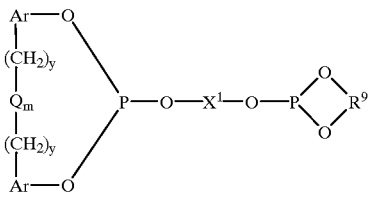

(XII)

wherein Ar, Q, $R^9$, $R^{10}$, $X^1$, m and y are as defined above. Most preferably $X^1$ represents a divalent aryl-$(CH_2)_y$—(Q)$_m$—$(CH_2)_y$-aryl radical wherein each y individually has a value of 0 or 1; m has a value of 0 or 1 and Q is —O—, —S— or —C($R^5$)$_2$— wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Of course any of the $R^3$, $R^4$, $R^8$, $R^9$, $R^{10}$, $X^1$, $X^2$, W, Q and Ar radicals of such organophosphites of formulas (II) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —Si($R^{12}$)$_3$; amino radicals such as —N($R^{12}$)$_2$; phosphine radicals such as -aryl-P($R^{12}$)$_2$; acyl radicals such as —C(O)$R^{12}$; acyloxy radicals such as —OC(O)$R^{12}$; amido radicals such as —CON($R^{12}$)$_2$ and —N($R^{12}$)COR$^{12}$; sulfonyl radicals such as —SO$_2R^{12}$; alkoxy radicals such as —OR$^{12}$; sulfinyl radicals such as —SOR$^{12}$; sulfenyl radicals such as —SR$^{12}$; phosphonyl radicals such as —P(O)($R^{12}$)$_2$; as well as, halogen, nitro, cyano, trifluoromethyl, hydroxy radicals, and the like, wherein each $R^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —N($R^{12}$)$_2$ each $R^{12}$ taken together can also represent a divalent bridging group that forms a heterocyclic radical with the nitrogen atom, and in amido substituents such as —(O)N($R^{12}$)$_2$ and —N($R^{12}$)COR$^{12}$ each $R^{12}$ bonded to N can also be hydrogen. Of course it is to be understood that ally of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —$OCH_2CH_2OCH_3$, —$(OCH_2CH_2)_2OCH_3$, —$(OCH_2CH_2)_3OCH_3$, and the like; aryloxy radicals such as phenoxy and the like, as well as silyl radicals such as —$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; arylphosphine radicals such as —$P(C_6H_5)_2$, and the like; acyl radicals such as —$C(O)CH_3$, —$C(O)C_2H_5$, —$C(O)C_6H_5$, and the like; carbonyloxy radicals such as —$C(O)OCH_3$ and the like; oxycarbonyl radicals such as —$O(CO)C_6H_5$, and the like; amido radicals such as —$CONH_2$, —$CON(CH_3)_2$, —$NHC(O)CH_3$, and the like; sulfonyl radicals such as —$S(O)_2C_2H_5$ and the like; sulfinyl radicals such as —$S(O)CH_3$ and the like; sulfenyl radicals such as —$SCH_3$, $SC_2H_5$, —$SC_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H_5)$, and the like.

Specific illustrative examples of organophosphorus ligands are described in U.S. Pat. No. 5,7786,517, the disclosure of which is incorporated herein by reference.

The metal-organophosphorus ligand complex catalysts are preferably in homogeneous form. For instance, preformed rhodium hydrido-carbonyl-organophosphorus ligand catalysts may be prepared and introduced into the reaction mixture of a particular process. More preferably, the metal-organophosphorus ligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst.

As noted above, the organophosphorus ligands can be employed as both the ligand of the metal-organophosphorus ligand complex catalyst, as well as, the free organophosphorus ligand that can be present in the reaction medium of the processes of this invention. In addition, it is to be understood that while the organophosphorus ligand of the metal-organophosphorus ligand complex catalyst and any excess free organophosphorus ligand preferably present in a given process of this invention are normally the same type of ligand, different types of organophosphorus ligands, as well as, mixtures of two or more different organophosphorus ligands may be employed for each purpose in any given process, if desired.

The amount of metal-organophosphorus ligand complex catalyst present in the reaction medium of a given process of this invention need only be that minimum amount necessary to provide the given metal concentration desired to be employed and which will furnish the basis for at least that catalytic amount of metal necessary to catalyze the particular process desired. In general, metal concentrations in the range of from about 1 part per million to about 10,000 parts per million, calculated as free metal, and ligand to metal mole ratios in the catalyst solution ranging from about 1:1 or less to about 200:1 or greater, should be sufficient for most processes.

As noted above, in addition to the metal-organophosphorus ligand complex catalysts, the processes of this invention and especially the hydroformylation process can be carried out in the presence of free organophosphorus ligand. While the processes of this invention may be carried out in any excess amount of free organophosphorus ligand desired, the employment of free organophosphorus ligand may not be absolutely necessary. Accordingly, in general, amounts of ligand of from about 1.1 or less to about 200, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the process, at any time and in any suitable manner, to maintain a predetermined level of free ligand in the reaction medium.

The reaction conditions of the hydroformylation processes encompassed by this invention many include any suitable type hydroformylation conditions heretofore employed for producing optically active and/or non-optically active formylesters. For instance, the total gas pressure of hydrogen, carbon monoxide and olefin starting compound of the hydroformylation process may range from about 1 to about 10,000 psia. In general, however, it is preferred that the process be operated at a total gas pressure of hydrogen, carbon monoxide and olefin starting compound of less than about 2000 psia and more preferably less than about 1000 psia. The minimum total pressure is limited predominately by the amount of reactants necessary to obtain a desired rate of reaction. More specifically the carbon monoxide partial pressure of the hydroformylation process of this invention is preferable from about 1 to about 1000 psia, and more preferably from about 3 to about 800 psia, while the hydrogen partial pressure is preferably about 5 to about 500 psia and more preferably from about 10 to about 300 psia. In general $H_2$:CO molar ratio of gaseous hydrogen to carbon monoxide may range from about 1:10 to 100:1 or higher, the more preferred hydrogen to carbon monoxide molar ratio being from about 1:10 to about 10:1. Further, the hydroformylation process may be conducted at a reaction temperature from about −25° C. to about 200° C. In general hydroformylation reaction temperatures of about 50° C. to about 120° C. are preferred for all types of olefinic starting materials. Of course it is to be understood that when non-optically active formylester products are desired, achiral type olefin starting materials and organophosphorus ligands are employed and when optically active formylester products are desired prochiral or chiral type olefin starting materials and organophosphorus ligands are employed. Of course, it is to be also understood that the hydroformylation reaction conditions employed will be governed by the type of formylester product desired.

The hydroformylation processes are conducted for a period of time sufficient to produce the desired formylundecanoates. The exact reaction time employed is dependent, in part, upon factors such as temperature, pressure, nature and proportion of starting materials, and the like. The reaction time will normally be within the range of from about one-half to about 200 hours or more, and preferably from less than about one to about 10 hours.

As indicated above, the processes of this invention are conducted in the presence of a nonpolar solvent and a polar solvent, or in the presence of a nonpolar solvent followed by mixing with a polar solvent, or in the presence of a nonpolar solvent followed by mixing with a second nonpolar solvent.

Depending on the particular catalyst and reactants employed, suitable nonpolar solvents include, for example, alkanes, cycloalkanes, alkenes, aldehydes, ketones, ethers, esters, amines, aromatics, silanes, silicones, carbon dioxide, and the like. Examples of unsuitable nonpolar solvents include fluorocarbons and fluorinated hydrocarbons. These are undesirable due to their high cost, risk of environmental pollution, and the potential of forming multiphases. In an embodiment, the one or more reactants, metal-organophosphorus ligand complex catalyst, and optionally free organophosphorus ligand exhibit sufficient solubility in the nonpolar solvent such that phase transfer agents or surfactants are not required.

Mixtures of one or more different nonpolar solvents may be employed if desired. The amount of nonpolar solvent employed is not critical to the subject invention and need only be that amount sufficient to provide the reaction medium with the particular metal concentration desired for a given process. In general, the amount of nonpolar solvent employed may range from about 5 percent by weight up to about 99 percent by weight or more based on the total weight of the reaction mixture.

Illustrative nonpolar solvents useful in this invention include, for example, propane, 2,2-dimethylpropane, butane, 2,2-dimethylbutane, pentane, isopropyl ether, hexane, triethylamine, heptane, octane, nonane, decane, isobutyl isobutyrate, tributylamine, undecane, 2,2,4-trimethylpentyl acetate, isobutyl heptyl ketone, diisobutyl ketone, cyclopentane, cyclohexane, isobutylbenzene, n-nonylbenzene, n-octylbenzene, n-butylbenzene, p-xylene, ethylbenzene, 1,3,5-trimethylbenzene, m-xylene, toluene, o-xylene, decene, dodecene, tetradecene, and heptadecanal. The solubility parameters of illustrative nonpolar solvents are given in the Table below.

TABLE

Solubility Parameters of Illustrative Non-Polar Solvents

| Non-Polar Solvent | $\delta_{Solvent}$ $(cal/cm^3)^{1/2}$ | $\delta_{Solvent}$ $(kJ/m^3)^{1/2}$ |
|---|---|---|
| Propane | 5.76 | 373 |
| 2,2-Dimethylpropane | 6.10 | 395 |
| Butane | 6.58 | 426 |
| 2,2-Dimethylbutane | 6.69 | 433 |
| Pentane | 7.02 | 454 |
| Isopropyl Ether | 7.06 | 457 |
| Hexane | 7.27 | 470 |
| Triethylamine | 7.42 | 480 |
| Heptane | 7.50 | 485 |
| Octane | 7.54 | 488 |
| Nonane | 7.64 | 494 |
| Decane | 7.72 | 499 |
| Isobutyl Isobutyrate | 7.74 | 501 |
| Tributylamine | 7.76 | 502 |
| Undecane | 7.80 | 505 |
| 2,2,4-Trimethylpentyl Acetate | 7.93 | 513 |
| Isobutyl Heptyl Ketone | 7.95 | 514 |
| Diisobutyl Ketone | 8.06 | 521 |
| Cyclopentane | 8.08 | 523 |
| Cyclohexane | 8.19 | 530 |
| n-Nonylbenzene | 8.49 | 549 |
| n-Octylbenzene | 8.56 | 554 |
| n-Butylbenzene | 8.57 | 554 |
| p-Xylene | 8.83 | 571 |
| Ethylbenzene | 8.84 | 572 |
| 1,3,5-Trimethylbenzene | 8.84 | 572 |
| m-Xylene | 8.88 | 574 |
| Toluene | 8.93 | 578 |
| o-Xylene | 9.06 | 586 |

The desired products of this invention can be selectively recovered by extraction and phase separation in a polar solvent. As indicated above, the polar solvent can be present with the nonpolar solvent during the reaction or the reaction product fluid can be contacted with a polar solvent after the reaction. The desired reaction product is preferably extracted from the reaction product fluid through the use of an appropriate polar solvent such that any extraction of the one or more reactants, metal-organophosphorus ligand complex catalyst, and optionally free organophosphorus ligand from the reaction product fluid is minimized or eliminated. In an embodiment, the polar solvent is an aqueous mixture preferably containing up to about 8 weight percent water, more preferably less than about 6 weight percent water, and most preferably less than about 4 weight percent water. In this embodiment, the processes of this invention are considered to be essentially "non-aqueous" processes, which is to say, any water present in the reaction mediums is not present in an amount sufficient to cause either the particular reaction or said medium to be considered as encompassing a separate aqueous or water phase or layer in addition to the organic phases. Depending on the particular desired products, suitable polar solvents include, for example, nitrites, lactones, alkanols, cyclic acetals, pyrrolidones, formamides, sulfoxides and the like. In another embodiment, the polar solvent is other than a combination of a primary alkanol and water.

Mixtures of one or more different polar solvents may be employed if desired. The Hildebrand solubility parameter for the polar solvent or mixtures of one or more different polar solvents should be less than about 13.5 $(cal/cm^2)^{1/2}$ or 873 $(kJ/m^3)^{1/2}$, preferably less than about 13.0 $(cal/cm^3)^{1/2}$ or 841 $(kJ/m^3)^{1/2}$, and more preferably less than about 12.5 $(cal/cm^3)^{1/2}$ or 809 $(kJ/m^3)^{1/2}$. The amount of polar solvent employed is not critical to the subject invention and need only be that amount sufficient to extract the one or more products from the reaction product fluid for any given process. In general, the amount of polar solvent employed may range from about 5 percent by weight up to about 50 percent by weight or more based on the total weight of the reaction product fluid.

Illustrative polar solvents useful in this invention include, for example, propionitrile, 1,3-dioxolane, 3-methoxypyropionitrile, N-methylpyrrolidone, N,N-dimethylformamide, 2-methyl-2-oxazoline, adiponitrile, acetonitrile, epsilon caprolactone, glutaronitrile, 3-methyl-2-oxazolidinone, water, dimethyl sulfoxide and sulfolane. The solubility parameters of illustrative polar solvents are given in the Table below.

TABLE

Solubility Parameters of Illustrative Polar Solvents

| Polar Solvent | $\delta_{Solvent}$ $(cal/cm^3)^{1/2}$ | $\delta_{Solvent}$ $(kJ/m^3)^{1/2}$ |
|---|---|---|
| Propionitrile | 10.73 | 694 |
| 1,3-Dioxolane | 11.33 | 733 |
| 3-Methoxypropionitrile | 11.37 | 735 |
| N-Methylpyrrolidone | 11.57 | 748 |
| N,N-Dimethylformamide | 11.76 | 761 |
| 2-Methyl-2-Oxazoline | 12.00 | 776 |
| Adiponitrile | 12.05 | 779 |
| Acetonitrile | 12.21 | 790 |
| E-Caprolactone | 12.66 | 819 |
| Sulfolane | 12.80 | 828 |
| Glutaronitrile | 13.10 | 847 |
| Dimethyl Sulfoxide | 13.10 | 847 |

TABLE-continued

Solubility Parameters of Illustrative Polar Solvents

| Polar Solvent | $\delta_{Solvent}$ $(cal/cm^3)^{1/2}$ | $\delta_{Solvent}$ $(kJ/m^3)^{1/2}$ |
| --- | --- | --- |
| 3-Methyl-2-Oxazolidinone | 13.33 | 862 |
| Water | 23.53 | 1522 |

Extraction to obtain one phase comprising the one or more reactants, metal-organophosphorus ligand complex catalyst, optionally free organophosphorus ligand and nonpolar solvent and at least one other phase comprising one or, more products and polar solvent is an equilibrium process. The relative volumes of the polar solvent (or extraction solution) and the nonpolar solvent or reaction product fluid in this extraction operation are determined in part by the solubility of the one or more reactants, metal-organophosphorus ligand complex catalyst, optionally free organophosphorus ligand and one or more products in the solvents used, and the amount of desired product to be extracted. For example, when the desired product is extracted, if the desired product to be extracted shows high solubility in the polar solvent and is present at a relatively low concentration in the reaction product fluid, it is possible to extract the desired product by using the polar solvent in a relatively small volume ratio to the reaction product fluid. The polar and nonpolar solvents described above may be used as extraction solvents.

Further, as the concentration of the desired product becomes high, it is usually required to increase the ratio of the polar solvent to the reaction product fluid for extracting the desired product from the reaction product fluid. When the desired product shows relatively low solubility in the polar solvent, the relative volume of the polar solvent or extraction solution will have to be increased. Generally, the volume ratio of the polar solvent or extraction solution to the reaction product fluid may be changed within a range of from about 20:1 to about 1:20.

In an embodiment, the products produced by the processes of this invention may contain sufficient polarity to make the products immiscible with the non-polar solvent. Phase separation may occur spontaneously or may be induced by a change in temperature or pressure or the addition of an additive, e.g., salt, or the evaporation of a solvent or combinations thereof. The addition of an external polar solvent to induce phase separation may not be required for certain processes of this invention.

Except as noted above, with respect to the extraction temperature, there is no merit in employing a temperature higher than the reaction temperature of the particular process, and desirable results can be obtained by employing an extraction temperature lower than the process reaction temperature. Depending on the particular process, extraction temperatures may range from about −80° C. or less to about 200° C. or greater.

The time for mixing the reaction product fluid with the polar solvent, i.e. the time before the phase separation, depends on the rate until the two-phases reach the equilibrium condition. Generally, such a time maybe varied from within one minute or less to a longer period of one hour or more.

The extraction process of this invention is in part an equilibrium process of an organophosphorus ligand dissolved in two separate liquid phases. The efficiency of this extraction process can be measured by a partition coefficient Kp1 of the organophosphorus ligand which is defined as follows:

$$Kp1 = \frac{\text{Concentration of organophosphorus ligand in the nonpolar phase after extraction}}{\text{Concentration of organophosphorus ligand in the polar phase after extraction}}$$

When the one or more desired products are partitioned between the polar phase and the nonpolar phase by the extraction process of this invention, the Kp1 value of the organophosphorus ligand can be maintained at a level greater than about 5, preferably greater than about 7.5, and more preferably greater than about 10, depending on the efficiency of the extraction process. If this Kp1 value is high, the organophosphorus ligand will preferentially distribute into the nonpolar phase. As used in Kp1, the concentration of organophosphorus ligand includes both free organophosphorus ligand and organophosphorus ligand complexed with the metal.

The extraction process of this invention is also in part an equilibrium process of one or more products dissolved in two separate liquid phases. The efficiency of this extraction process can be measured by a partition coefficient Kp2 of the one or more products which is defined as follows:

$$Kp2 = \frac{\text{Concentration of products in the nonpolar phase after extraction}}{\text{Concentration of products in the polar phase after extraction}}$$

When the one or more desired products are partitioned between the polar phase and the nonpolar phase by the extraction process of this invention the Kp1 value of the products can be maintained at a level less than about 2 preferably less than about 1.5 and more preferably less than about 1, depending on the efficiency of the extraction process. If this Kp2 value is low, the products will preferentially distribute into the polar phase.

The extraction process of this invention is further in part an equilibrium process of one or more organophosphorus ligand degradation products dissolved in two separate liquid phases. The efficiency of this extraction process can be measured by a partition coefficient Kp3 of the one or more organophosphorus ligand degradation products which is defined as follows:

$$Kp3 = \frac{\text{Concentration of organophosphorus ligand degradation products in the nonpolar phase after extraction}}{\text{Concentration of organophosphorus ligand degradation products in the polar phase after extraction}}$$

When the one or more organophosphorus ligand degradation products are partitioned between the polar phase and the nonpolar phase by the extraction process of this invention the Kp3 value of the organophosphorus ligand degradation products can be maintained at a level less than about 2, preferably less than about 1.5, and more preferably less than about 1, depending on the efficiency of the extraction process. If this Kp3 value is low, the organophosphorus ligand degradation products will preferentially distribute into the polar phase.

The extraction process of this invention is yet further in part an equilibrium process of one or more reaction byproducts dissolved in two separate liquid phases. The efficiency of this extraction process can be measured by a partition coefficient Kp4 of the one or more reaction byproducts which is defined as follows:

$$Kp4 = \frac{\text{Concentration of reaction byproducts in the nonpolar phase after extraction}}{\text{Concentration of reaction byproducts in the polar phase after extraction}}$$

When the one or more reaction byproducts are partitioned between the polar phase and the nonpolar phase by the extraction process of this invention, the Kp4 value of the reaction byproducts can be maintained at a level less than about 2, preferably less than about 1.5, and more preferably less than about 1, depending on the efficiency of the extraction process. If this Kp4 value is low, the reaction byproducts will preferentially distribute into the polar phase.

The extraction process of this invention is conducted in a manner such that three separation criteria are satisfied. The three criteria are referred to herein as extraction factors and are based on ratios of the partition coefficients defined above. The relationships embodied by the extraction factors include selectivity of the nonpolar phase for the organophosphorus ligand with respect to the product, selectivity of the nonpolar phase for the organophosphorus ligand with respect to the organophosphorus ligand degradation products, and selectivity of the nonpolar phase for the organophosphorus ligand with respect to the reaction byproducts. The three extraction factors ale set out below.

The extraction factor defining selectivity of the nonpolar phase for the organophosphorus ligand with respect to the one or more products is a partition coefficient ratio as follows:

$$Ef1 = \frac{\text{Partition coefficient } Kp1 \text{ of organophosphorus ligand}}{\text{Partition coefficient } Kp2 \text{ of one or more products}}$$

The Ef1 value for the above ratio is maintained at a level greater than about 2.5, preferably greater than about 3.0, and more preferably greater than about 3.5, depending on the efficiency of the extraction process. If this Ef1 value is high, the extraction selectivity will be high.

The extraction factor defining selectivity of the nonpolar phase for the organophosphorus ligand with respect to the one or more organophosphorus ligand degradation products is a partition coefficient ratio as follows:

$$Ef2 = \frac{\text{Partition coefficient } Kp1 \text{ of organophosphorus ligand}}{\text{Partition coefficient } Kp3 \text{ of one or more organophosphorus ligand degradation products}}$$

The Ef2 value for the above ratio is maintained at a level greater than about 2.5, preferably greater than about 3.0, and more preferably greater than about 3.5, depending on the efficiency of the extraction process. If this Ef2 value is high, the extraction selectivity will be high.

The extraction factor defining selectivity of the nonpolar phase for the organophosphorus ligand with respect to the one or more reaction byproducts is a partition coefficient ratio as follows:

$$Ef3 = \frac{\text{Partition coefficient } Kp1 \text{ of organophosphorus ligand}}{\text{Partition coefficient } Kp4 \text{ of one or more reaction byproducts}}$$

The Ef3 value for the above ratio is maintained at a level greater than about 2.5, preferably greater than about 3.0, and more preferably greater than about 3.5, depending on the efficiency of the extraction process. If this Ef3 value is high, the extraction selectivity will be high.

The extraction process of this invention may be conducted in one or more stages. The exact number of extraction stages will be governed by the best compromise between capital costs and achieving high extraction efficiency and ease of operability, as well as the stability of the starting materials and the desired reaction product to the extraction conditions. Also, the extraction process of this invention may be conducted in a batch or continuous fashion. When conducted continuously, the extraction may be conducted in a cocurrent or countercurrent manner or fractional countercurrent extraction may be used. Suitable fractional countercurrent extraction methods are disclosed in copending U.S. patent application Ser. Nos. (D-18040 and D-18041), filed on an even date herewith, the disclosures of which are incorporated herein by reference. In an embodiment, when separating the reaction product fluid, the reaction product fluid preferably contains at least 5 weight percent, preferably at least 10 weight percent, of one or more products.

Illustrative types of extractors that may be employed in this invention include, for example, columns, centrifuges, mixer-settlers, and miscellaneous devices. Extractors that could be utilized include unagitated columns, e.g., spray, baffle tray and packed, agitated columns, e.g., pulsed, rotary agitated and reciprocating plate, mixer-settlers, e.g., pump-settler, static mixer-settler and agitated mixer-settler, centrifugal extractors, e.g., those produced by Robatel, Luwesta, deLaval, Dorr Oliver, Bird and Podbielniak, and miscellaneous extractors, e.g., the emulsion phase contactor and hollow-fiber membrane. A description of these devices can be found in the Handbook of Solvent Extraction, Krieger Publishing Company, Malabar, Fla., 1991, the disclosure of which is incorporated herein by reference. As used in this invention, the various types of extractors may be combined in any combination to effect the desired extraction.

Following the extraction, the desired products, along with ally organophosphorus ligand degradation products and reaction byproducts, may be recovered by phase separation in which the polar phase comprising one or more products, organophosphorus ligand degradation products and reaction byproducts, is separated from the nonpolar phase. The phase separation techniques may correspond to those techniques heretofore employed in conventional processes, and can be accomplished in the extractor or in a separated liquid-liquid separation device. Suitable liquid-liquid separation devices include, but are not limited to, coalescers, cyclones and centrifuges. Typical equipment used for liquid-liquid phase separation devices are described in the Handbook of Separation process Technology, ISBN 0-471-89558-X, John Wiley & Sons, Inc., 1987, the disclosure of which is incorporated herein be reference.

From a free energy standpoint, to attain dissolution or miscibility of a phosphorous containing ligand in a particular solvent, the enthalpy of mixing should be as small as possible. The enthalpy of mixing ($\Delta H_m$) can be approximated by the Hildebrand equation (1)

$$\Delta H_m = \Phi_S \Phi_L V (\delta_{Solvent} - \delta_{Ligand})^2 \quad (1)$$

using the solubility parameters of the solvent ($\delta_{Solvent}$) and ligand ($\delta_{Ligand}$), where V is the molar volume of the mixture, and $\Phi_S$ and $\Phi_L$ are the volume fractions of the solvent and ligand, respectively. Based on equation (1), the ideal solvent for a ligand would have the same solubility parameter as the ligand itself, so that $\Delta H_m = 0$. However, for each ligand there is a characteristic range originating from its solubility parameter which encloses all liquids that are solvents for the ligand. In general, a solvent or a solvent blend having a solubility parameter that is within two units of the solubility parameter of the ligand will dissolve the ligand; however, relatively large deviations from this value can sometimes occur, especially if there are strong hydrogen bonding interactions. Therefore, equation (2)

$$\delta_{Solvent} - \delta_{Ligand} < 2.0 \ (cal/cm^3)^{1/2} \quad (2)$$

can be used semi-quantitatively to determine whether a liquid is a good solvent for a given ligand. In equation (2), $\delta_{Solvent}$ and $\delta_{Ligand}$ represent the solubility parameters of the solvent and ligand respectively.

For purposes of this invention, the solubility parameters for solvents can be calculated from equation (3)

$$\delta_{Solvent} = (\Delta H_v - RT) d / MW \quad (3)$$

in which $\Delta H_v$ is the heat of vaporization, R is a gas constant, T is temperature in degrees absolute, d is the density of the solvent, and MW is molecular weight of the solvent. The solubility parameters for a wide variety of solvents have been reported by K. L. Hoy, "New Values of the Solubility Parameters from Vapor Pressure Data," Journal of Paint Technology, 42, (1970), 76.

The heat of vaporization for phosphorous containing compounds cannot be easily measured since many of these compounds decompose at higher temperatures. Furthermore, since many phosphorous containing compounds are solids at room temperature, measurements of density are not convenient. The solubility parameters, in units of $(cal/cm^3)^{1/2}$, for phosphorus containing ligands can be calculated using equation (4)

$$\delta_{Ligand} = (\Sigma F_T + 135.1)/(0.01211 + \Sigma N_i V_{1i}) 1000 \quad (4)$$

from group contribution theory as developed by (1) K. L. Hoy, "New Values of the Solubility Parameters from Vapor Pressure Data," Journal of Paint Technology, 42, (1970), 76, and (2) L. Constantinou, R. Gani, J. P. O'Connell, "Estimation of the Acentric Factor and the Liquid Molar Volume at 298 K Using a New Group Contribution Method," Fluid Phase Equilibria, 103, (1995), 1 1. In equation (4), $\Sigma F_T$ is the sum of all the group molar attraction constants, and $\Sigma_i V_{1i}$ is the sum of all the first order liquid molar volume constants $V_{1i}$, which occur $N_i$ times. These methods have been expanded to include the group molar attraction constant of 79.4 $(cal/cm^3)^{1/2}$/mole and first order liquid molar volume constant of 0.0124 $m^3$/kmol for (>P—) derived from triphenylphosphine data found in T. E. Daubret, R. P. Danner, H. M. Sibul, and C. C. Stebbins "DIPPR Data Compilation of Pure Compound Properties," Project 801, Sponsor Release, July 1995, Design Institute for Physical Property Data, AIChE, New York, N.Y.

Accordingly illustrative formylester products include, for example, formylundecanoates such as 11-formylundecanoate, 10-formylundecanoate, 9-formylundecanoate and the like. Preferred formylesters are represented by the formula

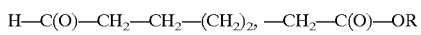

H—C(O)—CH$_2$—CH$_2$—(CH$_2$)$_2$, —CH$_2$—C(O)—OR wherein R is hydrogen or a substituted or unsubstituted hydrocarbon having a carbon atom number sufficient to render said formylester miscible in a polar solvent. Typically, R contains from 1 to about 6 or 7 carbon atoms. Illustrative of suitable substituted and unsubstituted formylester products include those permissible substituted and unsubstituted formylester compounds described in Beilsteins Handbuch der Organischen Chemie, Springer Verlag KG, 4$^{th}$ Edition, the pertinent portions of which are incorporated herein by reference.

Preferred formylester products include formylundecanoates and/or derivatives thereof. As used herein, derivatives of formylesters include, for example, formylacids and salts of formylacids. This invention is not intended to be limited in any manner by the permissible derivatives of formylesters.

In another embodiment, this invention includes batchwise or continuously generated reaction mixtures comprising:

(1) one or more substituted or unsubstituted formylesters and/or derivatives thereof;

(2) optionally one or more substituted or unsubstituted unsaturated esters and/or derivatives thereof; and (3) optionally castor oil and/or derivatives thereof;

wherein the weight ratio of component (1) to the sum of components (2) and (3) is greater than about 0.1; and the weight ratio of component (3) to the sum of components (1) and (2) is about 0 to about 100. Also, this invention includes reaction mixtures comprising one or more formylesters and/or derivatives thereof in which the reaction mixtures are prepared by the processes described herein. In accordance with this invention, the formylester product mixtures may be extracted and separated from the other components of the crude reaction mixtures in which the formylester mixtures are produced by phase separation as described above.

The formylesters produced by the processes of this invention can undergo further reaction(s) to afford desired derivatives thereof. Such permissible derivatization reactions can be carried out in accordance with conventional procedures known in the art. Illustrative derivatization reactions include, for example, hydrogenation, esterification, etherification, animation, alkylation, dehydrogenation, reduction, acylation, condensation, carboxylation, carbonylation, oxidation, cyclization, silylation and the like, including permissible combinations thereof. This invention is not intended to be limited in any manner by the permissible derivatization reactions of formylesters.

It is generally preferred to carry out the hydroformylation processes of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a nonpolar solvent, the metal-organophosphorus ligand complex catalyst, free organophosphorus ligand, and optionally a polar solvent; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; (d) mixing at least a portion of the reaction medium with a polar solvent to extract the desired aldehyde hydroformylation product(s) from the reaction medium; and (e) recovering the desired aldehyde product(s) by phase separation.

At the conclusion of (or during) the process of this invention, the desired formylesters may be recovered from the reaction mixtures used in the process of this invention. For instance, in a continuous liquid catalyst recycle process the portion of the liquid reaction mixture (containing formylester product, catalyst, etc.) removed from the reaction zone can be passed to a separation zone wherein the desired formylester product can be extracted and separated via phase separation from the liquid reaction mixture, and further purified if desired. The remaining catalyst containing liquid reaction mixture may then be recycled back to the reaction zone as may if desired any other materials, e.g., unreacted olefin, together with any hydrogen and carbon monoxide dissolved in the liquid reaction after separation thereof from the formylester product. Following phase separation in which a layer of the extraction fluid, e.g., polar solvent and one or more organophosphorus ligand degradation products, one or more reaction byproducts and one or more formylesters, is separated from a layer of the remaining reaction product fluid, the desired formylesters can then be separated from the undesired organophosphorus ligand degradation products and reaction byproducts by conventional methods such as distillation.

Hydrogenation Step or Stage

The hydrogenation processes involve converting one or more substituted or unsubstituted formylesters, e.g., 11-formylundecanoate, to one or more substituted or unsubstituted ester alcohols, e.g., 12-hydroxydodecanoate, or to one or more substituted or unsubstituted diols, e.g., 1,12-dodecanediols, in one or more steps or stages. As used herein, the term "hydrogenation" is contemplated to include, but is not limited to, all permissible hydrogenation processes which involve converting one or more substituted or unsubstituted formylesters, e.g., formylundecanoates, to one or more substituted or unsubstituted ester alcohols, e.g., hydroxydodecanoates, or to one or more substituted or unsubstituted diols, e.g., dodecanediols. In general, the hydrogenation step or stage comprises reacting one or more substituted or unsubstituted formylesters in the presence of a hydrogenation catalyst to produce one or more substituted or unsubstituted ester alcohols or one or more substituted or unsubstituted diols.

Formylundecanoates useful in the hydrogenation processes are known materials and can be prepared by the hydroformylation steps described above or by other conventional processes. Reaction mixtures comprising formylundecanoates may be useful herein. The amounts of formylundecanoates employed in the hydrogenation step is not narrowly critical and can be any amount sufficient to produce hydroxydodecanoates and/or dodecanediols, preferably in high selectivities. The formylundecanoates may be fed to the reactor in any convenient manner, such as in solution, or as a neat liquid.

The hydrogenation process may be carried out in one or more steps or stages and in any permissible sequence of steps or stages. In a one step process, hydroxydodecanoate and/or dodecanediols are the desired products leaving the reaction zone. In a multistep or multistage process, intermediate products are the major products leaving the individual reaction zones.

The particular hydrogenation reaction conditions are not narrowly critical and can be any effective hydrogenation conditions sufficient to produce the hydroxydodecanoates and/or dodecanediols. The reactors may be stirred tanks, tubular reactors and the like. The exact reaction conditions will be governed by the best compromise between achieving high catalyst selectivity, activity, lifetime and ease of operability as well as the intrinsic reactivity of the formylundecanoates in question and the stability of the formylundecanoates and the desired reaction product to the reaction conditions. Illustrative of certain reaction conditions that may be employed in the hydrogenation processes are described, for example, in P. N. Rylander, Hydrogenation Methods, Academic Press. New York, 1985, Chapter 5, the disclosure of which is incorporated herein by reference. Products may be recovered after a particular reaction zone and purified if desired although they may be introduced to the next reaction zone without purification. Recovery and purification may be by any appropriate means, which will largely be determined by the particular reactants employed.

The hydrogenation reaction can be conducted at a temperature of from about 0° C. to about 400° C. for a period of about 1 minute or less to about 4 hours or longer with the longer time being used at the lower temperature, preferably from about 50° C. to about 300° C. for about 1 minute or less to about 2 hours or longer, and more preferably at about 50° C. to about 25° C. for about 3 hours or less. The temperature should be sufficient for reaction to occur (which may vary with catalyst system) but not so high as to cause formylundecanoate decomposition or polymerization.

The hydrogenation reaction can be conducted over a wide range of pressures ranging from about 10 psig to about 4500 psig. It is preferable to conduct the hydrogenation reaction at pressures of from about 100 psig to about 2000 psig. The hydrogenation reaction is preferably effected in the liquid or vapor states or mixtures thereof. The total pressure will depend on the catalyst system used. The hydrogen partial pressure should be chosen to maximize the efficiency of the hydrogenation catalyst and obtain the desired selectivity and degree of conversion.

The hydrogenation reaction step or stage involve the use of a catalyst. Such catalysts are known in the art and can be used in conventional amounts. Of course mixtures of catalysts can also be employed if desired. The amount of catalyst employed will be dependent on the hydrogenation reaction conditions employed and the amount should be sufficient to obtain the desired selectivity and degree of conversion. In general, the amount of catalyst employed should be sufficient to enable a conversion of formylundecanoates to hydroxydodecanoates and/or dodecanediols of at least about 5 percent, preferably at least about 20 percent, and more preferably at least about 50 percent.

As indicated above, the substituted and unsubstituted hydroxydodecanoates and/or dodecanediols produced by the hydrogenation step can be separated by conventional techniques such as filtration, distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the hydrogenation reaction step.

Illustrative substituted and unsubstituted hydroxydodecanoates that can be prepared by the hydrogenation stage or step of this invention include one or more of the following: methyl 12-hydroxydodecanoate, ethyl 12-hydroxydodecanoate, propyl 12-hydroxydodecanoate, and butyl 12-hydroxydodecanoate, including mixtures comprising one or more of the above ester alcohols. Preferred ester alcohols are represented by the formula

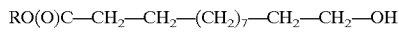

wherein R is hydrogen or a substituted or unsubstituted hydrocarbon having from 1 to about 6 or 7 carbon atoms. Illustrative of suitable substituted and unsubstituted ester alcohols include those permissible substituted and unsubstituted ester alcohols which are described in Dictionary of Organic Compounds, Sixth Edition, Chapman and Hall, Cambridge, 1996, the pertinent portions of which are incorporated herein by reference.

Illustrative substituted and unsubstituted diols that can be prepared by the hydrolysis stage or step of this invention include one or more of the following: 1,12-dodecanediol, 2-methyl-1,11-undecanediol, 3-methyl-1,11-undecanediol, including mixtures comprising one or more of the above diols. Preferred diols are represented by the formula

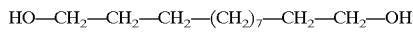

wherein R is hydrogen or a substituted or unsubstituted hydrocarbon having from 1 to about 6 or 7 carbon atoms. Illustrative of suitable substituted and unsubstituted diols include those permissible substituted and unsubstituted diols which are described in Dictionary of Organic Compounds, Sixth Edition, Chapman and Hall, Cambridge, 1996, the pertinent portions of which are incorporated herein by reference.

The hydroxydodecanoates and dodecanediols described herein are useful in a variety of applications, such as the manufacture of synthetic fibers, plastics, bristles, film, coatings, synthetic leather, plasticizers and paint vehicles, crosslinking agent for polyurethanes, and the like. The hydroxydodecanoates call be reacted with polyols, such as diethylene glycol, 1,4-butanediol, neopentyl glycol, 1,6-hexanediol, trimethylolpropane, and the like, to give polyester polyols which can improve the flexibility and the hydrolytic resistance of coatings. The polyester polyols can be reacted with diisocyanates in the preparation of urethane elastomers. Self condensation of the ester alcohol can lead to a thermoplastic polyester with a low solubility parameter. Hydrolysis of the ester alcohol to the acid alcohol can lead to a crosslinker having dual reactivity for liquid coatings and powder coatings as well as adhesives.

Reductive Amination Step or Stage

The reductive Amination processes involve converting one or more substituted or unsubstituted formylesters. e.g., 11-formylundecanoate, to one or more substituted or unsubstituted aminoesters, e.g., 12-aminododecanoate, in one or more steps or stages. As used herein, the term "reductive amination" is contemplated to include, but is not limited to, all permissible reductive amination processes which involve converting one or more substituted or unsubstituted formylesters, e.g., formylundecanoates, to one or more substituted or unsubstituted aminoesters, e.g., aminododecanoate. In general, the reductive amination step or stage comprises reacting one or more substituted or unsubstituted formylesters optionally in the presence of a reductive amination catalyst to produce one or more substituted or unsubstituted aminoesters.

Formylundecanoates useful in the reductive amination processes are known materials and can be prepared by the hydroformylation steps described above or by other conventional processes. Reaction mixtures comprising formylundecanoates may be useful herein. The amounts of formylundecanoates employed in the reductive amination stop is not narrowly critical and can be any amount sufficient to produce aminododecanoates, preferably in high selectivities.

The reductive amination process may be carried out in one or more steps or stages and in any permissible sequence of steps or stages. In a one step process, aminododecanoate is the desired product leaving the reaction zone. In a multistep or multistage process, intermediate products are the major products leaving the individual reaction zones.

The particular reductive amination reaction conditions are not narrowly critical and can be any effective reductive amination condition is sufficient to produce the aminododecanoates. The reactors may be stirred tanks, tubular reactors and the like. The exact reaction conditions will be governed by the best compromise between achieving high catalyst selectivity, activity, lifetime and ease of operability, as well as the intrinsic reactivity of the formylundecanoates in question and the stability of the formylundecanoates and the desired reaction product to the reaction conditions. Illustrative of certain reaction conditions that may be employed in the reductive amination processes are described, for example, in U.S. Pat. Nos. 2,777,873, 4,766,237, 5,068,398 and 5,700,934, the disclosures of which are incorporated herein by reference. Products may be recovered after a particular reaction zone and purified if desired although they may be introduced to the next reaction zone without purification. Recovery and purification may be by any appropriate means, which will largely be determined by the particular reactants employed.

The reductive amination reaction can be conducted at a temperature of from about 0° C. to about 400° C. for a period of about 1 minute or less to about 4 hours or longer with the longer time being used at the lower temperature, preferably from about 50° C. to about 300° C. for about 1 minute or less to about 2 hours or longer, and more preferably at about 50° C. to about 250° C. for about 1 minute or less to about 2 hours or longer. The temperature should be sufficient for reaction to occur (which may vary with catalyst system) but not so high as to cause formylundecanoate decomposition or polymerization.

The reductive amination reaction can be conducted over a wide range of pressures ranging from about 10 psig to about 4500 psig. It is preferable to conduct the reductive amination reaction at pressures of from about 100 psig to about 2000 psig. The reductive amination reaction is preferably effected in the liquid or vapor states or mixtures thereof. The total pressure will depend on the catalyst system used. The hydrogen partial pressure should be chosen to maximize the lifetime of the amination catalyst and obtain the desired selectivity and degree of conversion.

Ammonia is preferably employed as the aminating agent in these reactions in conventional amounts, preferably in excess amounts, and it may be fed to the reactor in a variety of ways, including as a liquid, and a gas, in solution in for example water, or as ammonium salts in solution or in some other appropriate manner, e.g., urea. Any excess ammonia is preferably separated off after reductive amination is completed. The formylundecanoates may be fed to the reactor in any convenient manner, such as in solution, or as a neat liquid.

Some of the reaction steps or stages may involve the use of a catalyst. Such catalysts are known in the art and can be used in conventional amounts. Catalysts useful in the reductive amination stage or step include, for example, Raney nickel, Raney cobalt, nickel on silica/alumina, palladium on carbon, platinum on carbon, rhodium on alumina, and the like. Of course mixtures of catalysts can also be employed if desired. The amount of catalyst employed will be dependent on the reductive amination reaction conditions employed and the amount should be sufficient to obtain the desired selectivity and degree of conversion. In general, the amount of catalyst employed should be sufficient to enable a conversion of formylundecanoates to aminododecanoate of at least about 5 percent, preferably at least about 20 percent, and more preferably at least about 50 percent.

As indicated above, the substituted and unsubstituted aminododecanoates produced by the reductive amination step can be separated by conventional techniques such as filtration, distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the reductive amination reaction step.

Illustrative aminododecanoates that can be prepared by the processes of this invention include, for example, 12-aminododecanoate, methyl 12-aminododecanoate, ethyl 12-aminododecanoate, propyl 12-aminododecanoate, and butyl 12-aminododecanoate. Preferred aminoesters are represented by the formula

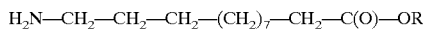

$$H_2N-CH_2-CH_2-CH_2-(CH_2)_7-CH_2-C(O)-OR$$

wherein R is hydrogen or a substituted or unsubstituted hydrocarbon having from 1 to about 6 or 7 carbon atoms. Illustrative of suitable substituted and unsubstituted aminododecanoates include those permissible substituted and unsubstituted aminododecanoates which are described in Dictionary of Organic Compounds, Sixth Edition, Chapman and Hall, Cambridge, 1996, the pertinent portions of which are incorporated herein by reference.

Oxidation Stage or Step

The oxidation stare or step of this invention involves converting one or more substituted or unsubstituted formylesters, e.g., 11-formylundecanoate, to one or more substituted or unsubstituted acidoesters, e.g., monoalkyl ester of 1,12-dodecanedioic acid. The oxidation stage or step of this invention may be conducted in one or more steps or stages, preferably a one step process.

As used herein, the term "oxidation" is contemplated to include all permissible oxidation processes which involve converting one or more substituted or unsubstituted formylesters, e.g., formylundecanoates, to one or more substituted or unsubstituted acidoesters, e.g., monoalkyl esters of dodecanedioic acid. In general, the oxidation step or stage comprises reacting one or more substituted or unsubstituted formylesters, e.g., 11-formylundecanoate, with an oxygen source, e.g., air, essentially pure oxygen or oxygen-enriched air containing at least about 50% oxygen, optionally in the presence of an oxidation catalyst or an oxidation catalyst and a promoter, and optionally an initiator, to produce one or more substituted or unsubstituted acidoesters, e.g., monoalkyl esters of dodecanedioic acid.

Formylundecanoates useful in the oxidation process are described above and can be prepared by the methods described above. The amount of formylundecanoates employed in the oxidation step is not narrowly critical and can be any amount sufficient to produce monoalkyl esters of dodecanedioic acid, preferably in high selectivities.

The oxidation process may be carried out in one or more steps or stages and in any permissible sequence of steps or stages. In a one step process, monoalkyl esters of dodecanedioic acid are the desired products leaving the reaction zone. In a multistep or multistage process, intermediate products are the major products leaving the individual reaction zones. Of course some overlap of individual transformations may occur, so that in a two stage process, some transformations may occur in different order.

The particular oxidation reaction conditions are not narrowly critical and can be any effective oxidation conditions sufficient to produce monoalkyl esters of dodecanedioic acid. The reactors may be stirred tanks, tubular reactors and the like. The exact reaction conditions will be governed by the best compromise between achieving high selectivity, activity, lifetime and ease of operability, as well as the intrinsic reactivity of the formylundecanoates in question and the stability of the formylundecanoates to the reaction conditions. Illustrative of certain reaction conditions that may be employed in the oxidation processes are described, for example, in U.S. Pat. Nos. 8,331,121, 5,840,959, 4,537, 987 and 5,817,870, the disclosures of which are incorporated herein by reference. Products may be recovered after a particular reaction zone and purified if desired although they may be introduced to the next reaction zone without purification. Recovery and purification may be by any appropriate means, which will largely be determined by the particular formylundecanoate starting material employed.

The oxidation reaction can be conducted at a temperature of from about 0° C. to about 200° C. for a period of about 1 minute or less to about 4 hours or longer with the longer time being used at the lower temperature, preferably from about 10° C. to about 150° C. for about 1 minute or less to about 2 hours or longer, and more preferably at about 20° C. to about 125° C. for about 1 minute or less to about 2 hours or longer. The temperature should be sufficient for reaction to occur (which may vary with catalyst system) but not so high as to cause formylundecanoate decomposition.

The oxidation reaction can be conducted over a wide range of pressures ranging from about 10 psig to about 2000 psig. It is preferable to conduct the oxidation reaction at pressures of from about 10 psig to about 1000 psig. The oxidation reaction is preferably effected in the liquid or vapor states or mixtures thereof. The total pressure will depend on the temperature and other reaction conditions.

The oxidation reaction can be conducted using a variety of oxidants. Illustrative oxidants include, for example, molecular oxygen, molecular oxygen mixed with an inert gas such as nitrogen, molecular oxygen in air, hydrogen peroxide, peracetic acid and the like. The oxidant can be employed in conventional amounts.

The oxidation step or stage may involve the use of a catalyst. Such catalysts are known in the art and can be homogeneous or heterogeneous. Catalysts useful in the oxidation stage or step include, for example, palladium supported on carbon, palladium on supports such as alumina or silica, platinum on carbon, alkali metal hydroxide, cobalt acetate, manganese acetate, bismuth molybdates, molybdenum-vanadium oxides, manganese porphyrin complexes, homogeneous molybdenum complexes, and the like. Of course mixtures of oxidation catalysts can also be employed if desired. The amount of catalyst employed will be dependent on the oxidation reaction conditions employed and the amount should be sufficient to obtain the desired selectivity and degree of conversion. In general, the amount of catalyst employed should be sufficient to enable a conversion of formylundecanoate to monoalkyl ester of dodecanedioic acid of at least about 5 percent, preferably at least about 20 percent, and more preferably at least about 50 percent.

The oxidation process may also be conducted in the presence of a promoter. As used herein, the term "promoter", when used in the context of oxidation, means a material added to the oxidation reaction mixture to impart a promotion effect to catalytic activity, e.g., rate, product selectivity, and/or catalyst stability (mechanical or dimensional strength of the catalyst). Illustrative promoters include, for example, alkali metal hydroxide, acetate salts, Group VII metals, rare earth oxides, alkaline earth metals, and the like. The promoter may be present in the oxidation reaction mixture either alone or incorporated into the catalyst structure. The desired promoter will depend on the nature of the catalysts. The concentration of the promoter employed will depend upon the details of the catalyst system employed.

The oxidation process may also be conducted in the presence of an initiator. As used herein, the term "initiator", when used in the context of oxidation, means a material added to the oxidation reaction mixture to initiate the reaction by starting, for example, a free radical chain reaction. Illustrative initiators include, for example, sodium persulfate, ammonium persulfate, benzoyl peroxide, perbenzoic acid, tertiary-butyl hydroperoxide, alkyl peroxide, peracids, peresters, azobisisobutyronitrile, redox systems such as hydrogen peroxide/iron acetate, and the like. The initiator may be present in the oxidation reaction mixture either alone or in addition to a catalyst. The desired initiator will depend on the nature of the reaction system and reaction conditions. The concentration of the initiator employed will depend upon the details of the reaction system employed.

Illustrative substituted and unsubstituted monoalkyl esters of dodecanedioic acid that can be prepared by the oxidation stage or step of this invention include one or more of the following: monoalkyl ester of 1,12-dodecanedioic acid, methyl ester of 1,12-dodecanedioic acid, ethyl ester of 1,12-dodecanedioic acid, propyl ester of 1,12-dodecanedioic acid, and butyl ester of 1,12-dodecanedioic acid, including mixtures comprising one or more of the above monoalkyl esters of dodecanedioic acid. Preferred acidoesters are represented by the formula

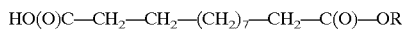

$$HO(O)C\text{—}CH_2\text{—}CH_2\text{—}(CH_2)_7\text{—}CH_2\text{—}C(O)\text{—}OR$$

wherein R is hydrogen or a substituted or unsubstituted hydrocarbon having from 1 to about 6 or 7 carbon atoms. Illustrative of suitable substituted and unsubstituted monoalkyl esters of dodecanedioic acid include those permissible substituted and unsubstituted monoalkyl esters of dodecanedioic acid which are described in Dictionary of Organic Compounds, Sixth Edition, Chapman and Hall, Cambridge. 1996, the pertinent portions of which are incorporated herein by reference.

Recovery and purification of monoalkyl esters of dodecanedioic acid may be by any appropriate means, and may include phase separation, extraction, precipitation, absorption, crystallization, membrane separation, derivative formation and other suitable means. Distillation may result in decomposition at atmospheric pressure and is therefore undesirable. Crystallization is a preferred purification method. The subsequent derivatization of the monoalkyl ester of dodecanedioic acid may be conducted without the need to separate the monoalkyl ester of dodecanedioic acid from the other components of the crude reaction mixtures.

In an embodiment, the oxidation stage or step of this invention may be carried out in a liquid oxidation reactor such as described, for example, in copending U.S. patent application Ser. No. 09/063,675, filed on Apr. 21, 1998, the disclosure of which is incorporated herein by reference.

Hydrolysis Step or Stave

The hydrolysis process involves converting (when reductive amination is employed) one or more substituted or unsubstituted aminoesters, e.g., 12-aminododecanoate, to one or more substituted or unsubstituted aminoacids, e.g., 12-aminododecanoic acid, in one or more steps or, stages, or converting (when oxidation is employed) one or more substituted or unsubstituted acidoesters, e.g., monoalkyl ester of 1,12-dodecanedioic acid, to one or more substituted or unsubstituted diacids, e.g., 1,12-dodecanedioic acid, in one or more steps or stages. As used herein, the term "hydrolysis" is contemplated to include, but is not limited to, all permissible hydrolysis processes which involve converting one or more substituted or unsubstituted aminoesters to one or more substituted or unsubstituted aminoacids or which involve converting one or more substituted or unsubstituted acidoesters to one or more substituted or unsubstituted diacids. In general, the hydrolysis step or stage comprises reacting one or more substituted or unsubstituted aminoesters, e.g., aminododecanoates, optionally in the presence of a catalyst to produce one or more substituted or unsubstituted aminoacids, e.g., aminododecanoic acids, or reacting one or more substituted or unsubstituted acidoesters, e.g., monoalkyl esters of dodecanedioic acid, optionally in the presence of a catalyst to produce one or more substituted or unsubstituted diacids, e.g., dodecanedioic acids.

Aminododecanoates useful in the hydrolysis process are known materials and can be prepared by the reductive amination step described above or by other conventional processes. Reaction mixtures comprising aminododecanoates may be useful herein. Monoalkyl esters of dodecanedioic acid useful in the hydrolysis process are known materials and can be prepared by the oxidation step described above or by other conventional processes. Reaction mixtures comprising monoalkyl esters of dodecanedioic acid may be useful herein. The amounts of aminododecanoates and monoalkyl esters of dodecanedioic acid employed in the hydrolysis step are not narrowly critical and can be any amounts sufficient to produce either aminododecanoic acids or dodecanedioic acids, preferably in high selectivities.

The hydrolysis process may be carried out in one or more steps or stages and in any permissible sequence of steps or stages. In a one step process, aminododecanoic acids or dodecanedioic acids are the desired products leaving the reaction zone. In a multistep or multistage process, intermediate products are the major products leaving the individual reaction zones.

The particular hydrolysis reaction conditions are not narrowly critical and can be any effective hydrolysis conditions sufficient to produce either aminododecanoic acids or dodecanedioic acids. The reactors may be stirred tanks, tubular reactors and the like. The exact reaction conditions will be governed by the best compromise between achieving high catalyst selectivity, activity, lifetime and ease of operability, as well as the intrinsic reactivity of the aminododecanoates or monoalkyl esters of dodecanedioic acid in question and the stability of the aminododecanoates or monoalkyl esters of dodecanedioic acid and the desired reaction product to the reaction conditions. Illustrative of certain reaction conditions that may be employed in the hydrolysis process are described, for example, in U.S. Pat. No. 4,950,429, the disclosure of which is incorporated herein by reference. Products may be recovered after a particular reaction zone and purified if desired although they may be introduced to the next reaction Zone without purification. Recovery and purification may be by any appropriate means, which will largely be determined by the particular reactants employed.

The hydrolysis reaction can be conducted at a temperature of from about 0° C. to about 400° C. for a period of about 1 minute or less to about 4 hours or longer with the longer time being used at the lower temperature, preferably from about 50° C. to about. 300° C. for about 1 minute or less to about 2 hours or longer, and more preferably at about 50° C. to about 250° C. for about 1 minute or less to about 2 hours or longer. The temperature should be sufficient for reaction to occur (which may vary with catalyst system) but not so high as to cause aminododecanoate or monoalkyl ester of dodecanedioic acid decomposition.

The hydrolysis reaction can be conducted over a wide range of pressures ranging from about 10 psig to about 4500 psig. It is preferable to conduct the hydrolysis reaction at pressures of from about 10 psig to about 2000 psig. The hydrolysis reaction is preferably effected in the liquid or vapor states or mixtures thereof. The total pressure will depend on the catalyst system used.

Some of the reaction steps or stages may involve the use of a catalyst. Such catalysts ale known in the art and can be homogeneous or heterogeneous. Catalysts useful in the hydrolysis stage or step are known materials and include, for example, Group IVB metal oxides, metallic phosphates which may or may not have a cyclic structure, metallic polyphosphates which may or may not have a condensed structure, Group VIB metal containing substances, and the like. Typical ester hydrolysis catalysts include acids and acid resins. See, for example, in U.S. Pat. No. 4,950,429, supra. Of course mixtures of hydrolysis catalysts can also be employed if desired. The amount of catalyst employed will be dependent on the hydrolysis reaction conditions employed and the amount should be sufficient to obtain the desired selectivity and degree of conversion. In general, the amount of catalyst employed should be sufficient to enable a conversion to aminododecanoic acid or dodecanedioic acid of at least about 5 percent, preferably at least about 20 percent, and more preferably at least about 50 percent.

As indicated above, the substituted and unsubstituted aminododecanoic acids or dodecanedioic acids produced by the hydrolysis step can be separated by conventional techniques such as distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the hydrolysis reaction step. Illustrative epsilon caprolactams that can be prepared by the processes of this invention are described above.

Illustrative substituted and unsubstituted aminododecanoic acids that can be prepared by the hydrolysis stage or step of this invention include one or more of the following: 12-aminododecanedioic acid, 11-amino-10-methylundecanedioic acid, including mixtures comprising one or more of the above aminoacids. Preferred aminoacids are represented by the formula

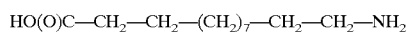

wherein R is hydrogen or a substituted or unsubstituted hydrocarbon having from 1 to about 6 or 7 carbon atoms. Illustrative of suitable substituted and unsubstituted aminoacids include those permissible substituted and unsubstituted aminoacids which are described in Dictionary of Organic Compounds, Sixth Edition, Chapman and Hall, Cambridge, 1996, the pertinent portions of which are incorporated herein by reference.

Illustrative substituted and unsubstituted dodecanedioic acids that can be prepared by the hydrolysis stage or step of this invention include one or more of the following: 1,12-dodecanedioic acid, 2-methyl-1,11-undecanedioic acid, including mixtures comprising one or more of the above diacids. Preferred diacids are represented by the formula

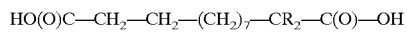

wherein R is hydrogen or a substituted or unsubstituted hydrocarbon having from 1 to about 6 or 7 carbon atoms. Illustrative of suitable substituted and unsubstituted diacids include those permissible substituted and unsubstituted diacids which are described in Dictionary of Organic Compounds, Sixth Edition, Chapman and Hall, Cambridge, 1996, the pertinent portions of which are incorporated herein by reference.

The aminododecanoic acids and dodecanedioic acids described herein are useful in a variety of applications, such as the manufacture of synthetic fibers (especially nylon 12 from polymerization of 12-aminododecanoic acid and nylon 6,12 from copolymerization of 1,12-dodecanedioic acid and hexamethylenediamine), plastics, bristles, film, coatings, synthetic leather, plasticizers and paint vehicles, crosslinking agent for polyurethanes, and the like. The manufacture of polyamides is a preferred application.

The processes of this invention can be conducted in a batch or continuous fashion, with recycle of unconsumed starting materials if required. The reaction can be conducted in a plurality of reaction zones, in series or in parallel or it may be conducted batchwise or continuously in an elongated tubular zone or series of such zones. For example, a back-mixed reactor may be employed in series with a multistaged reactor with the backmixed reactor being first. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product by phase separation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more reaction steps and more than one reactive stages. The exact number of reaction steps and reactive stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate this invention. It is to be understood that all manipulations were carried out under a nitrogen atmosphere unless otherwise stated. Also, all examples were carried out at ambient temperature unless otherwise stated.

The ligands set out below are used in the following examples.

Ligand A

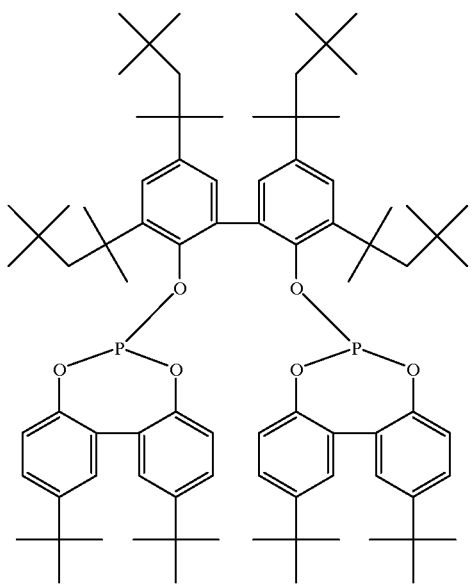

Ligand B

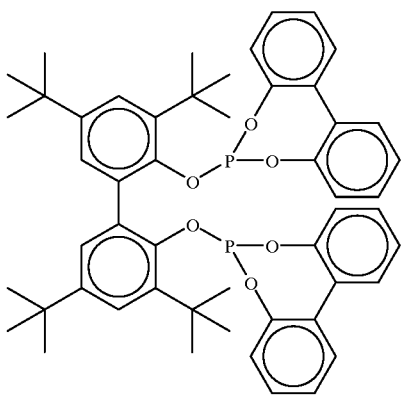

EXAMPLE 1

To a magnetically stirred 100 milliliter stainless steel autoclave under nitrogen was charged 20 milliliters of a solution containing 572 parts per million of rhodium (acetylacetonato)dicarbonylrhodium(I), and 0.63 weight percent of Ligand A in heptane.

The mixture was then heated to 70° C. and the pressure allowed to reach equilibrium. To this mixture was then added 1.0 milliliter of ethyl 10-undecenoate. The reactor was then sealed. The reactor was then placed under $H_2$:CO and held at a pressure between 95 and 100 psig for 5 hours. At this point, the contents of the reactor were discharged into a nitrogen purged vessel. Analysis of the discharged solution indicated (96% conversion of the ethyl 10-undecenoate. In addition, normal to branched ratio, defined as the amount of normal or straight chain isomer/amount of branched isomers, for the aldehyde product was 42.

EXAMPLE 2

At room temperature, 10 milliliters of the discharged reaction solution from Example 1 was transferred to a nitrogen purged vessel. To the vessel was then added an equal volume of acetonitrile. The mixture was vigorously shaken for several minutes then allowed to settle and phase separate. The layers were then analyzed for rhodium content and hydroformylation product. The partition coefficient of the catalyst and the product, as defined bay Kpartition= amount of material in the heptane phase/amount of material in the acetonitrile phase, was then determined for each component. Kpartition for rhodium was found to be 170, and Kpartition for the hydroformylation product was found to be 0.25.

The extraction factor of the catalyst for one phase relative to the product, as defined by extraction factor=Kpartition rhodium/Kpartition product, was 680.

EXAMPLE 3

A solution of rhodium dicarbonyl acetylacetonate (10.1 milligrams; 0.039 mmol) and Ligand B (98.1 milligrams; 0.117 mmol) in heptane (18 grams) was placed in a Parr reactor and activated for about 1 hour at 70° C. and 100 psi of syngas (CO/$H_2$ 1:1). Ethyl 10-undecenoate (1.2 grams) and octane (0.8 grams, internal standard) were charged to the autoclave and hydroformylated at 70° C. and 100 psi of syngas. The CO/$H_2$ ratio was maintained 1:1 during the course of reaction. After 20 hours the reaction mixture was analyzed by gas chromatography. The starting material was completely consumed and selectivity to the aldehyde products was 92% with the n/i ratio of 43.

EXAMPLE 4

The autoclave containing the hydroformylation mixture from Example 3 was cooled to ambient temperature and its contents were discharged to give a one phase system. A portion of the reaction solution (2 milliliters) was extracted with acetonitrile (2 milliliters). The phases were separated and the content of ethyl 11-formylundecanoate product was determined in both phases by gas chromatography. The partition coefficient of the product, as defined by Kpartition= amount of product in the heptane phase/amount of product in the acetonitrile phase, was determined to be 0.25.

EXAMPLE 5

A solution of rhodium dicarbonyl acetylacetonate (10.1 mg; 0.039 mmol) and Ligand B (98.1 mg; 0.117 mmol) in heptane (18 g) was placed in a 80 ml Parr reactor and activated for about 1 hour at 70° C. and 100 psi of syngas (CO/$H_2$1:1). Methyl 10-undecenoate (1.2 g; 6.06 mmol) and octane (0.8 g, internal standard) were charged to the autoclave. Hydroformylation was carried out at 70° C. and 100 psi of syngas with the CO/$H_2$ ratio of 1:1. The reaction mixture was monitored by gas chromatography. After 20 hours, the starting material was completely consumed and selectivity to the aldehyde products was 80% with n/iso ratio of 33.

EXAMPLE 6

The autoclave containing the hydroformylation mixture from Example 5 was cooled to ambient temperature and its content was discharged to give a one phase system. A portion of the reaction solution (2 milliliters) was extracted with acetonitrile (2 milliliters). The phases were separated, and the content of methyl 11-formylundecanoate product in each phase was determined by gas chromatography. The partition coefficient of the product, as defined by Kpartition=amount of product in the heptane phase/amount of product in the acetonitrile phase, was determined to be 0.19.

EXAMPLE 7

A solution of rhodium dicarbonyl acetylacetonate (10.1 milligrams; 0.039 mmol) and Ligand B (98.1 milligrams; 0.117 mmol) in heptane (18 grams) was placed in a Parr reactor and activated for about 1 hour at 70° C. and 100 psi of syngas (CO/$H_2$ 1:1). Butyl 10-undecenoate (1.2 grams) and octane (0.8 grams, internal standard) were charged to the autoclave and hydroformylated at 70° C. and 100 psi of syngas. The pressure of syngas was maintained 100 psi during the course of reaction. The reaction was followed by gas chromatography. After 20 hours the starting material was completely consumed and selectivity to the aldehyde products was 90% with the n/i ratio of 43.

EXAMPLE 8

The autoclave containing the hydroformylation mixture from Example 7 was cooled to room temperature and its contents were discharged to give a one phase system. A portion of the reaction solution (2 milliliters) was extracted with acetonitrile (2 milliliters). The phases were separated and the content of butyl 11-formylundecanoate product was determined in both phases by gas chromatography. The partition coefficient of the product, as defined by Kpartition= amount of product in the heptane phase/amount of product in the acetonitrile phase, was determined to be 0.56.

EXAMPLE 9

A solution of rhodium dicarbonyl acetylacetonate (30.3 mg; 0.117 mmol) and Ligand A (453 mg; 0.352 mmol) in heptane (24 g) was placed in a 160 ml Parr reactor and activated for about 1 hour at 70° C. and 100 psi of syngas (CO/$H_2$ 1:1). Methyl 10-undecenoate (24 g; 121 mmol) and octane (12 g, internal standard) were charged to the autoclave. Hydroformylation was carried out at 70° C. and 100 psi of syngas with the CO/$H_2$ ratio of 1:1. The reaction mixture was monitored by GC. After 18 hrs the starting material was completely consumed and selectivity to the aldehyde products was 86% with n/iso ratio of 35.

A portion of the reaction solution (5 mL) was diluted with heptane (10 mL), shaken at room temperature under nitrogen with acetonitrle (13 mL) and allowed to settle. Two phases with approximately equal volumes were analyzed for rhodium and the hydroformylation product. The partition coefficient of the catalyst and the product defined as Kpartition=amount of material in the heptane phase/amount of material in the acetonitrile phase was determined for each component. Kpartition for rhodium was found to be 166, and Kpartition for the hydroformylation product was found to be 0.17. The extraction factor of the catalyst for one phase relative to the product, defined as extraction factor= Kpartition rhodium/Kpartition product was 976.

The solvent was removed from the acetonitrile layer, and the crude product was crystallized from hexane (15 mL) at −5° C. to give 1.4 g (72% yield) of purified methyl 11-formylundecanoate with n/iso ratio of 147.

$^1$H NMR spectrum in D-chloroform (chemical shifts in ppm are relative to trimethylsilane as external standard): 1.23 (m, 14 H, seven methylene groups), 1.57 (m, 4H, two methylene groups), 2.25 (t, J=7.4 Hz, 2H, one methylene group), 2.29 (doublet of triplets, $J_1$=7.4 Hz, $J_2$=1.8 Hz, 2H, one methylene group), 3.62 (s, 3H, methoxy group), 971 (t, J=1.8 Hz, 1H, aldehyde proton). $^{13}$C NMR spectrum in D-chloroform (chemical shifts in ppm are relative to tetramethylsilane as external standard): 21.86, 24.73, 28.91, 28.94, 29.01, 29.12, 29.41, 29.14, 33.86, 43.68 (ten methylene groups), 51.23 (methoxy group), 174.10 (ester carbonyl group), 202.70 (formyl group).

EXAMPLE 10

Methyl 11-formylundecanoate (1.0 g; 4.39 mmol), isopropanol (20 milliliters) and chromium modified Raney nickel (0.1 grams) were placed in a 80 milliliter Parr reactor and hydrogenated at 80° C. and 500 psi of hydrogen. After 2 hours, all the starting material was consumed, and the reaction resulted in methyl 12-hydroxydodecanoate with 98% selectivity. The product was isolated as a white solid after filtration, solvent evaporation and drying in vacuum.

$^1$H NMR spectrum in D-chloroform (chemical shifts in ppm are relative to trimethylsilane as external standard): 1.26 (m, 14 H, seven methylene groups), 1.55 (m, 2H, one methylene group), 1.60 (m, 2H, one methylene group), 1.69 (s, 1H, hydroxyl group), 2.29 (t, J=7.6 Hz, 2H, one methylene group), 3.63 (t, J=6.7 Hz, 2H, one methylene group), 3.66 (s, 3H, methoxy group).

$^{13}$C NMR spectrum in D-chloroform (chemical shifts in ppm are relative to tetramethylsilane as external standard):

24.87, 25.16, 29.06, 29.16, 29.33, 29.34, 29.41, 29.48, 32.68, 34.04, 62.94 (eleven methylene groups), 51.40 (methoxy group), 174.33 (ester carbonyl group).

EXAMPLE 11

Air was sparged in a solution of methyl 11-formylundecanoate (1.0 gram; 4.39 mmol) in heptane (20 milliliters) at 50° C. The reaction was followed by gas chromatography. After 3 hours, greater than 97% of the starting material was oxidized. The product was crystallized from the same solution at room temperature and isolated as a white solid with greater than 99.5% purity.

$^1$H NMR spectrum in D-chloroform (chemical shifts in ppm are relative to tetramethylsilane as external standard): 1.27 (m, 12 H, six methylene groups), 1.60 (m, 4H, two methylene group), 2.30 (t, J=7.7 Hz, 2H, one methylene group), 2.34 (t, J=7.5 Hz, 2H, one methylene group), 3.66 (s, 3H methoxy group).

EXAMPLE 12

Methyl 11-formylundecanoate (1.4 grams; 6.14 mmol) in methanol (5 milliliters) was placed at room temperature in a 160 milliliter Parr reactor containing methanol (60 milliliters) ammonia (3.13 grams; 184 mmol) and nickel (65 wt. %) on silica/alumina (0.5 grams) and stirred for 10 minutes. Then hydrogen was charged and the reaction continued at 6° C. and 1,000 psi. Analysis by gas chromatography after 20 hours showed that all the starting material was consumed, and the reaction resulted in methyl 12-aminododecanoate in 91% yield. The catalyst was separated by filtration, the solvent was evaporated and a crude product was purified by crystallization from hexane.

$^1$H NMR spectrum in D-ethanol (chemical shifts in ppm are relative to tetramethylsilane as external standard): 1.30 (m, 14 H, eight methylene groups), 1.59 (m, 4H, two methylene groups), 2.29 (t, J=7.5 Hz, 2H, one methylene group), 3.62 (s, 3H, methoxy group). Mass spectrum: 229 (M$^+$).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for separating one or more organophosphorus ligand degradation products, one or more reaction byproducts and one or more products, said products comprising one or more formylesters and/or derivatives thereof, from a reaction product fluid comprising one or more unreacted unsaturated reactants, said unsaturated reactants comprising one or more unsaturated esters and/or derivatives thereof, a metal-organophosphorus ligand complex catalyst, optionally free organophosphorus ligand, said one or more organophosphorus ligand degradation products, said one or more reaction byproducts, said one or more products, a nonpolar solvent and a polar solvent, wherein said process comprises (1) mixing said reaction product fluid to obtain by phase separation a nonpolar phase comprising said one or more unreacted reactants, said metal-organophosphorus ligand complex catalyst, said optionally free organophosphorus ligand and said nonpolar solvent and a polar phase comprising said one or more organophosphorus ligand degradation products, said one or more reaction byproducts, said one or more products and said polar solvent, and (2) recovering said polar phase from said nonpolar phase; wherein (i) the selectivity of the nonpolar phase for the organophosphorus ligand with respect to the one or more products is expressed by the following partition coefficient ratio Ef1:

$$Ef1 = \frac{\text{Partition coefficient } Kp1 \text{ of organophosphorus ligand}}{\text{Partition coefficient } Kp2 \text{ of one or more products}}$$

in which said partition coefficient Kp1 is the ratio of the concentration of organophosphorus ligand in the nonpolar phase after extraction to the concentration of organophosphorus ligand in the polar phase after extraction, said partition coefficient Kp2 is the ratio of the concentration of products in the nonpolar phase after extraction to the concentration of products in the polar phase after extraction, and said Ef1 is a value greater than about 2.5, (ii) the selectivity of the nonpolar phase for the organophosphorus ligand with respect to the one or more organophosphorus ligand degradation products is expressed by the following partition coefficient ratio Ef2:

$$Ef2 = \frac{\text{Partition coefficient } Kp1 \text{ of organophosphorus ligand}}{\text{Partition coefficient } Kp3 \text{ of one or more organophosphorus ligand degradation products}}$$

in which said partition coefficient Kp1 is as defined above, said partition coefficient Kp3 is the ratio of the concentration of organophosphorus ligand degradation products in the nonpolar phase after extraction to the concentration of organophosphorus ligand degradation products in the polar phase after extraction, and said Ef2 is a value greater than about 2.5, and (iii) the selectivity of the nonpolar phase for the organophosphorus ligand with respect to the one or more reaction byproducts is expressed by the following partition coefficient ratio Ef3:

$$Ef3 = \frac{\text{Partition coefficient } Kp1 \text{ of organophosphorus ligand}}{\text{Partition coefficient } Kp4 \text{ of one or more reaction byproducts}}$$

in which said partition coefficient Kp1 is as defined above, said partition coefficient Kp4 is the ratio of the concentration of reaction byproducts in the nonpolar phase after extraction to the concentration of reaction byproducts in the polar phase after extraction, and said Ef3 is a value greater than about 2.5.

2. A process for separating one or more organophosphorus ligand degradation products, one or more reaction byproducts and one or more products, said products comprising one or more formylesters and/or derivatives thereof, from a reaction product fluid comprising one or more unreacted unsaturated reactants, said unsaturated reactants comprising one or more unsaturated esters and/or derivatives thereof, a metal-organophosphorus ligand complex catalyst, optionally free organophosphorus ligand, said one or more organophosphorus ligand degradation products, said one or more reaction byproducts, said one or more products and a nonpolar solvent, wherein said process comprises (1) mixing said reaction product fluid with a polar solvent to obtain by phase separation a nonpolar phase comprising said one or more unreacted unsaturated reactants, said metal-organophosphorus ligand complex catalyst, said optionally free organophosphorus ligand and said nonpolar solvent and a polar phase comprising said one or more organophosphorus ligand degradation products, said one or more reaction byproducts, said one or more products and said polar solvent, and (2) recovering said polar phase from said nonpolar phase, wherein (i) the selectivity of the nonpolar phase for the organophosphorus ligand with respect to the one or more products is expressed by the partition coefficient ratio Ef1 defined in claim 1 which is a value greater than about 2.5), (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

3. A process for producing one or more products, said products comprising one or more formylesters and/or derivatives thereof, comprising: (1) reacting one or more unsaturated reactants, said unsaturated reactants comprising one or more unsaturated esters and/or derivatives thereof, in the presence of a metal-organophosphorus ligand complex catalyst, optionally free organophosphorus ligand, a nonpolar solvent and a polar solvent to form a multiphase reaction product fluid, and (2) separating said multiphase reaction product fluid to obtain at least one nonpolar phase comprising one or more unreacted unsaturated reactants, said metal-organophosphorus ligand complex catalyst, said optionally free organophosphorus ligand and said nonpolar solvent and at least one polar phase comprising one or more organophosphorus ligand degradation products, one or more reaction byproducts, said one or more products and said polar solvent; wherein (i) the selectivity of the at least one nonpolar phase for the organophosphorus ligand with respect to the one or more products is expressed by the partition coefficient ratio Ef1 defined in claim 1 which is a value greater than about 2.5, (ii) the selectivity of the at least one nonpolar phase for the organophosphorus ligand with respect to the one or more organophosphorus ligand degradation products is expressed by the partition coefficient ratio Ef2 defines in claim 1 which is a value greater than about 2.5, and (iii) the selectivity of the at least one nonpolar phase for the organophosphorus ligand with respect to the one or more reaction byproducts is expressed by the partition coefficient ratio Ef3 defined in claim 1 which is a value greater than about 2.5.

4. A process for producing one or more products, said products comprising one or more formylesters and/or derivatives thereof, comprising: (1) reacting one or more unsaturated reactants, said unsaturated reactants comprising one or more unsaturated esters and/or derivatives thereof in the presence of a metal-organophosphorus ligand complex catalyst, optionally free organophosphorus ligand and a nonpolar solvent to form a reaction product fluid; (2) mixing said reaction product fluid with a polar solvent to form a multiphase reaction product fluid; and (3) separating said multiphase reaction product fluid to obtain at least one nonpolar phase comprising one or more unreacted unsaturated reactants, said metal-organophosphorus ligand complex catalyst said optionally free organophosphorus ligand and said nonpolar solvent, and at least one polar phase comprising one or more organophosphorus ligand degradation products, one or more reaction byproducts, said one or more products and said polar solvent; wherein (i) the selectivity of the at least one nonpolar phase for the organophosphorus ligand with respect to the one or more products is expressed by the partition coefficient ratio Ef1 defined in claim 1 which is a value greater than about 2.5, (ii) the selectivity of the at least one nonpolar phase for the organophosphorus ligand with respect to the one or more organophosphorus ligand degradation products is expressed by the partition coefficient ratio Ef2 defined in claim 1 which is a value greater than about 2.5. and (iii) the selectivity of the at least one nonpolar phase for the organophosphorus ligand with respect to the one or more reaction byproducts is expressed by the partition coefficient ratio Ef3 defined in claim 1 which is a value greater than about 2.5.

5. A process for separating one or more organophosphorus ligand degradation products, one or more reaction byproducts and one or more products, said products comprising one or more formylesters and/or derivatives thereof, from a reaction product fluid comprising one or more unreacted unsaturated reactants, said unsaturated reactants comprising one or more unsaturated esters and/or derivatives thereof, a metal-organophosphorus ligand complex catalyst, optionally free organophosphorus ligand, said one or more organophosphorus ligand degradation products said one or more reaction byproducts, said one or more products, a first nonpolar solvent and a second nonpolar solvent, wherein said process comprises (1) mixing said reaction product fluid to obtain by phase separation a nonpolar phase comprising said one or more unreacted unsaturated reactants, said metal-organophosphorus and complex catalyst, said optionally free organophosphorus ligand, said first nonpolar solvent and said second nonpolar solvent and a polar phase comprising said one or more organophosphorus ligand degradation products, said one or more reaction byproducts and said one or more products, and (2) recovering said polar phase from said nonpolar phase; wherein (i) the selectivity of the nonpolar phase for the organophosphorus ligand with respect to the one or more products is expressed by the partition coefficient ratio Ef1 defined in claim 1 which is a value greater than about 2.5), (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

6. A process for separating one or more organophosphorus ligand degradation products, one or more reaction byproducts and one or more products, said products comprising one or more formylesters and/or derivatives thereof, from a reaction product fluid comprising one or more unreacted unsaturated reactants, said unsaturated reactants comprising one or more unsaturated esters and/or derivatives thereof, a metal-organophosphorus ligand complex catalyst, optionally flee organophosphorus ligand, said one or more organophosphorus ligand degradation products, said one or more reaction byproducts, said one or more products and a first nonpolar solvent, wherein said process comprises (1) mixing said reaction product fluid with a second nonpolar solvent to obtain by phase separation a nonpolar phase comprising said one or more unreacted unsaturated reactants, said metal-organophosphorus ligand complex catalyst, said optionally free organophosphorus ligand, said first nonpolar solvent and said second nonpolar solvent and a polar phase comprising said one or more organophosphorus ligand degradation products, said one or more reaction byproducts and said one or more products, and (2) recovering said polar phase from said nonpolar phase; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

7. A process for producing one or more products, said products comprising one or more formylesters and/or derivatives thereof, comprising: (1) reacting one or more unsaturated reactants, said unsaturated reactants comprising one or more unsaturated esters and/or derivatives thereof, in the presence of a metal-organophosphorus ligand complex catalyst, optionally free organophosphorus ligand, a first nonpolar solvent and a second nonpolar solvent to form a multiphase reaction product fluid; and (2) separating said multiphase reaction product fluid to obtain at least one nonpolar phase comprising one, or more unreacted unsaturated reactants, said metal-organophosphorus ligand complex catalyst, said optionally free organophosphorus ligand, said first nonpolar solvent and said second nonpolar solvent and at least one polar phase comprising one or more organophosphorus ligand degradation products, one or more reaction byproducts and said one or more products; wherein (i) the selectivity of the at least one nonpolar phase for the organophosphorus ligand with respect to the one or more products is expressed by the partition coefficient ratio Ef1 defined in claim 1 which is a value greater than about 2.5, (ii) the selectivity of the at least one nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the at least one nonpolar phase for the organophosphorus ligand with respect to the one or more reaction byproducts is expressed by the partition coefficient ratio Ef3 defined in claim 1 which is a value greater than about 2.5.

8. A process for producing one or more products, said products comprising one or more formylesters and/or derivatives thereof, comprising: (1) reacting one or more unsaturated reactants, said unsaturated reactants comprising one or more unsaturated esters and/or derivatives thereof, in the presence of a metal-organophosphorus ligand complex catalyst, optionally free organophosphorus ligand and a first nonpolar solvent to form a reaction product fluid; (2) mixing said reaction product fluid with a second nonpolar solvent to form a multiphase reaction product fluid; and (3) separating said multiphase reaction product fluid to obtain at least one nonpolar phase comprising one or more unreacted unsaturated reactants, said metal-organophosphorus ligand complex catalyst, said optionally free organophosphorus ligand, said first nonpolar solvent and said second nonpolar solvent and at least one polar phase comprising one or more organophosphorus ligand degradation products, one or more reaction byproducts and said one or more products; wherein (i) the selectivity of the at least one nonpolar phase for the organophosphorus ligand with respect to the one or more products is expressed by the partition coefficient ratio Ef1 defined in claim 1 which is a value greater than about 2.5, (ii) the selectivity of the at least one nonpolar phase for the organophosphorus ligand with respect to the one or more organophosphorus ligand degradation products is expressed by the partition coefficient ratio Ef2 defined in claim 1 which is a value greater than about 2.5. and (iii) the selectivity of the at least one nonpolar phase for the organophosphorus ligand with respect to the one or more reaction byproducts is expressed by the partition coefficient ratio Ef3 defined in claim 1 which is a value greater than about 2.5.

9. A process for separating one or more organophosphorus ligand degradation products, one or more reaction byproducts and one or more products, said products comprising one or more formylesters and/or derivatives thereof, from a reaction product fluid comprising one, or more unreacted unsaturated reactants, said unsaturated reactants comprising one or more unsaturated esters and/or derivatives thereof, a metal-organophosphorus ligand complex catalyst, optionally free organophosphorus ligand, said one or more organophosphorus ligand degradation products, said one or more reaction byproducts, said one or more products and a nonpolar solvent, wherein said process comprises (1) mixing said reaction product fluid to obtain by phase separation a nonpolar phase comprising said one or more unreacted unsaturated reactants, said metal-organophosphorus ligand complex catalyst, said optionally free organophosphorus ligand and said nonpolar solvent and a polar phase comprising said one or more organophosphorus ligand degradation products, said one or more reaction byproducts and said one or more products, and (2) recovering said polar phase from said nonpolar phase; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

10. A process for producing one or more products, said products comprising one or more formylesters and/or derivatives thereof, comprising: (1) reacting one or more unsaturated reactants, said unsaturated reactants comprising one or more unsaturated esters and/or derivatives thereof, in the presence of a metal-organophosphorus ligand complex catalyst, optionally free organophosphorus ligand and a nonpolar solvent to form a multiphase reaction product fluid; and (2) separating said multiphase reaction product fluid to obtain at least one nonpolar phase comprising one or more unreacted unsaturated reactants, said metal-organophosphorus ligand complex catalyst, said optionally free organophosphorus ligand and said nonpolar solvent and at least one polar phase comprising one or more organophosphorus ligand degradation products, one or more reaction byproducts and said one or more products; wherein (i) the selectivity of the at least one nonpolar phase for the organophosphorus ligand with respect to the one or more products is expressed by the partition coefficient ratio Ef1 defined in claim 1 which is a value greater than about 2.5, (ii) the selectivity of the at least one nonpolar phase for the organophosphorus ligand with respect to the one or more organophosphorus ligand degradation products is expressed by the partition coefficient ratio Ef2 defined in claim 1 which is a value greater than about 2.5. and (iii) the selectivity of the at least one, nonpolar phase for the organophosphorus ligand with respect to the one or more reaction byproducts is expressed by the partition coefficient ratio Ef3 defined in claim 1 which is a value greater than about 2.5.

11. The process of claim 1 wherein Ef1 is a value of greater than about 3.0, Ef2 is a value of greater than about 3.0, and Ef3 is a value of greater than about 3.0.

12. The process of claim 1 wherein the one or more unsaturated esters comprise esters of undecenoic acid.

13. The process of claim 12 wherein the one or more esters of undecenoic acid are derived from castor oil.

14. The process of claim 1 wherein said nonpolar solvent is selected from alkanes, cycloalkanes, alkenes, aldehydes, ketones, ethers, esters, amines, aromatics, silanes, silicones, carbon dioxide, and mixtures thereof.

15. The process of claim 1 wherein said polar solvent is selected from nitriles, lactones, alkanols, cyclic acetals, pyrrolidones, formamides, sulfoxides, and mixtures thereof.

16. The process of claim 14 wherein said nonpolar solvent is selected from propane, 2,2-dimethylpropane, butane, 2,2-dimethylbutane, pentane, isopropyl ether, hexane, triethylamine, heptane, octane, nonane, decane, isobutyl isobutyrate, tributylamine, undecane, 2,2,4-trimethylpentyl acetate, isobutyl heptyl ketone, diisobutyl ketone, cyclopentane, cyclohexane, isobutylbenzene, n-nonylbenzene, n-octylbenzene, n-butylbenzene, p-xylene, ethylbenzene, 1,3,5-trimethylbenzene, m-xylene, toluene, o-xylene, decene, dodecene, tetradecene, heptadecanal, and mixtures thereof.

17. The process of claim 15 wherein said polar solvent is selected from propionitrile, 1,3-dioxolane, 3-methoxypropionitrile, 1-methyl-2-pyrrolidinone, N,N-dimethylformamide, 2-methyl-2-oxazoline, adiponitrile, acetonitrile, epsilon caprolactone, glutaronitrile, 3-methyl-2-oxazolidinone, dimethyl sulfoxide, sulfolane, and mixtures thereof.

18. The process of claim 1 wherein said metal-organophosphorus ligand complex catalyst comprises rhodium complexed with an organophosphorus ligand represented by the formula:

(i) a triorganophosphine ligand represented by the formula:

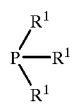

wherein $R^1$ is the same or different and represents a substituted or unsubstituted monovalent hydrocarbon radical containing from 1 to 24 carbon atoms or 1 greater;

(ii) a monoorganophosphite represented by the formula:

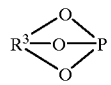

wherein $R^3$ represents a substituted or unsubstituted trivalent hydrocarbon radical containing from 4 to 40 carbon atoms or greater;

(iii) a diorganophosphite represented by the formula:

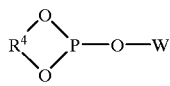

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

wherein each $R^8$ is the same or different and represents a substituted or unsubstituted monovalent hydrocarbon radical; and (v) an organopolyphosphite containing two or more tertiary (trivalent) phosphorus atoms represented by the formula:

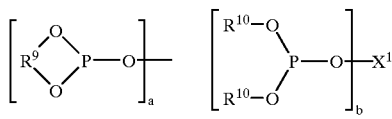

wherein $X^1$ represents a substituted or unsubstituted n-valent hydrocarbon bridging radical containing from 2 to 40 carbon atoms, each $R^9$ is the same or different and represents a divalent hydrocarbon radical containing from 4 to 40 carbon atoms, each $R^{10}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

19. A reaction mixture comprising one or more substituted or unsubstituted products, said products comprising one or more formylesters and/or derivatives thereof, in which said reaction mixture is prepared by the process of claim 3.

20. The process of claim 3 further comprising derivatizing the one or more formylesters.

21. The process of claim 20 in which the derivatizing reaction comprises hydrogenation, esterification, etherification, amination, alkylation, dehydrogenation, reduction, acylation, condensation, carboxylation, carbonylation, oxidation, cyclization, reductive amination, silylation, hydrolysis, polymerization, copolymerization and permissible combinations thereof.

22. The process of claim 3 further comprising subjecting said one or more formylesters to reductive amination optionally in the presence of a reductive amination catalyst to produce one or more aminoesters, subjecting said one or more aminoesters to hydrolysis optionally in the presence of a hydrolysis catalyst to produce one or more aminoacids, and subjecting said one or more aminoacids to polymerization to produce one or more polyamides.

23. The process of claim 3 further comprising subjecting said one or more formylesters to oxidation optionally in the presence of an oxidation catalyst to produce one or more acidoesters, subjecting said one or more acidoesters to hydrolysis optionally in the presence of a hydrolysis catalyst to produce one or more diacids, and subjecting said one or more diacids to copolymerization with one or more diamines to produce one or more polyamides.

24. The process of claim 3 further comprising subjecting said one or more formylesters to hydrogenation optionally in the presence of a hydrogenation catalyst to produce one or more ester alcohols and/or one or more diols.

* * * * *